(12) United States Patent
Schumacher et al.

(10) Patent No.: US 11,250,177 B2
(45) Date of Patent: *Feb. 15, 2022

(54) SYSTEMS AND METHODS FOR MODELING, ANALYZING, DETECTING, AND MONITORING FLUID NETWORKS

(71) Applicant: 3M INNOVATIVE PROPERTIES COMPANY, St. Paul, MN (US)

(72) Inventors: Jennifer F. Schumacher, Woodbury, MN (US); Saber Taghaeeyan, Maple Grove, MN (US); Ronald D. Jesme, Plymouth, MN (US); Andrew P. Bonifas, Alberta (CA); Nicholas G. Amell, Burnsville, MN (US); Brock A. Hable, Woodbury, MN (US); Golshan Golnari, Roseville, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 322 days.

This patent is subject to a terminal disclaimer.

(21) Appl. No.: 16/328,179

(22) PCT Filed: Jul. 31, 2017

(86) PCT No.: PCT/US2017/044722
§ 371 (c)(1),
(2) Date: Feb. 25, 2019

(87) PCT Pub. No.: WO2018/044461
PCT Pub. Date: Mar. 8, 2018

(65) Prior Publication Data
US 2019/0236219 A1    Aug. 1, 2019

Related U.S. Application Data

(60) Provisional application No. 62/381,944, filed on Aug. 31, 2016.

(51) Int. Cl.
*G06F 30/13* (2020.01)
*G06Q 50/06* (2012.01)
(Continued)

(52) U.S. Cl.
CPC .......... *G06F 30/13* (2020.01); *F15B 19/007* (2013.01); *G06F 16/9024* (2019.01);
(Continued)

(58) Field of Classification Search
CPC ...... G06Q 50/06; G01M 3/28; G01M 3/2807; E03B 11/02; F15B 19/007; Y02A 20/15;
(Continued)

(56) References Cited

U.S. PATENT DOCUMENTS 5,646,863 A    7/1997   Morton
7,497,957 B2 *  3/2009   Frank .................. C02F 1/008
                                                      210/739
(Continued)

FOREIGN PATENT DOCUMENTS

CN    102855526    1/2013
CN    103322416    9/2013
(Continued)

OTHER PUBLICATIONS

T.Y. B. Wolf, W. E. Hart, J. Saia, "Discrete Sensor Placement Problems in Distribution Networks", pp. 1385-1396 (Year: 2005).*
(Continued)

*Primary Examiner* — Kibrom K Gebresilassie
(74) *Attorney, Agent, or Firm* — Yufeng Dong

(57) ABSTRACT

Systems and methods are provided for optimally determining sensor or infrastructure placement in a fluid network, for determining an anomaly of interest in the fluid network, and
(Continued)

for determining sensor coverage in a fluid network, which are based on a model of the fluid network represented by a directed graph.

19 Claims, 20 Drawing Sheets

(51) Int. Cl.
| | | |
|---|---|---|
| *G06F 30/18* | (2020.01) | |
| *F15B 19/00* | (2006.01) | |
| *G06F 30/20* | (2020.01) | |
| *G06F 16/901* | (2019.01) | |
| *E03B 11/02* | (2006.01) | |
| *G01M 3/28* | (2006.01) | |
| *G01N 21/94* | (2006.01) | |
| *G01N 33/00* | (2006.01) | |

(52) U.S. Cl.
CPC .............. *G06F 30/18* (2020.01); *G06F 30/20* (2020.01); *G06Q 50/06* (2013.01); *E03B 11/02* (2013.01); *G01M 3/28* (2013.01); *G01M 3/2807* (2013.01); *G01N 21/94* (2013.01); *G01N 33/0031* (2013.01); *Y02A 20/15* (2018.01)

(58) Field of Classification Search
CPC ......... G06F 30/18; G06F 30/20; G01N 21/94; G01N 33/0031
See application file for complete search history.

(56) References Cited

U.S. PATENT DOCUMENTS

| | | | |
|---|---|---|---|
| 7,596,470 B2 | 9/2009 | Kim | |
| 8,175,859 B1 | 5/2012 | Wu | |
| 8,327,306 B2 | 12/2012 | Oh | |
| 8,958,917 B2 | 2/2015 | Wolfe | |
| 9,720,422 B2 | 8/2017 | Pantelides | |
| 9,797,799 B2 | 10/2017 | Zhang | |
| 10,161,749 B1 * | 12/2018 | Wu | G01N 33/18 |
| 10,795,382 B2 * | 10/2020 | Shafiee | G06F 30/20 |
| 2007/0284293 A1 | 12/2007 | Pitchford | |
| 2011/0191267 A1 * | 8/2011 | Savic | G06Q 50/06 |
| | | | 705/412 |
| 2012/0013483 A1 | 1/2012 | Jung | |
| 2013/0211601 A1 | 8/2013 | Cheng | |
| 2013/0211797 A1 * | 8/2013 | Scolnicov | G06Q 50/06 |
| | | | 703/2 |
| 2015/0020606 A1 | 1/2015 | Rahamim | |
| 2015/0095000 A1 | 4/2015 | Patil | |
| 2015/0204701 A1 | 7/2015 | Klicpera | |
| 2015/0308919 A1 | 10/2015 | Zhang | |

FOREIGN PATENT DOCUMENTS

| | | | |
|---|---|---|---|
| CN | 103808907 | 5/2014 | |
| CN | 103838959 | 6/2014 | |
| CN | 104061443 | 9/2014 | |
| WO | WO 2014/092918 A1 | 6/2014 | |
| WO | WO-2014092918 A1 * | 6/2014 | G06Q 10/04 |
| WO | WO 2014/135953 A2 | 9/2014 | |
| WO | WO 2017-030809 | 2/2017 | |
| WO | WO 2017-030812 | 2/2017 | |
| WO | WO 2017-030869 | 2/2017 | |
| WO | WO 2018-044462 | 3/2018 | |
| WO | WO 2018-044590 | 3/2018 | |

OTHER PUBLICATIONS

G. Golnari, Y. Li, Z. L. Zhang, "Pivotality of Nodes in Reachability Problems Using Avoidance and Transit Hitting Time Metrics" 2015, pp. 1073-1078. (Year: 2015).*

Eliades D G et al: "A Fault Diagnosis and Security Framework for Water Systems", IEEE Transactions on Control Systems Technology, IEEE Service Center, New York, NY, US, vol. 18, No. 6, Nov. 1, 2010 (Nov. 1, 2010), pp. 1254-1265.

Golnari, "Pivotality of Nodes in Reachability Problems Using Avoidance and Transit Hitting Time Metrics", The 7th Annual Workshop on Simplifying Complex Networks for Practitioners (Simplex), May 2015, pp. 1073-1078.

Golnari, "Revisiting Non-Progressive Influence Models: Scalable Influence Maximization in Social Networks", The 31st Conference on Uncertainty in Artificial Intelligence (UAI) proceeding, 2015, pp. 1-11.

Steinitz, "Optimal Camera Placement", Electrical Engineering and Computer Sciences Department University of California, Berkeley, Technical Report No. UCB/EECS-2012-69, May 2012, pp. 1-39.

Valiant, "The complexity of enumeration and reliability problems", Society for Industrial and Applied Mathematics Journal on Computing, Aug. 1979, vol. 8, No. 3, pp. 410-421.

Whittle, "Sensor Networks for Monitoring and Control of Water Distribution Systems", The 6th International Conference on Structural Health Monitoring of Intelligent Infrastructure, Dec. 2013, pp. 1-13.

International Search Report for PCT International Application No. PCT/US2017/044722, dated Nov. 8, 2017, 3 pages.

\* cited by examiner

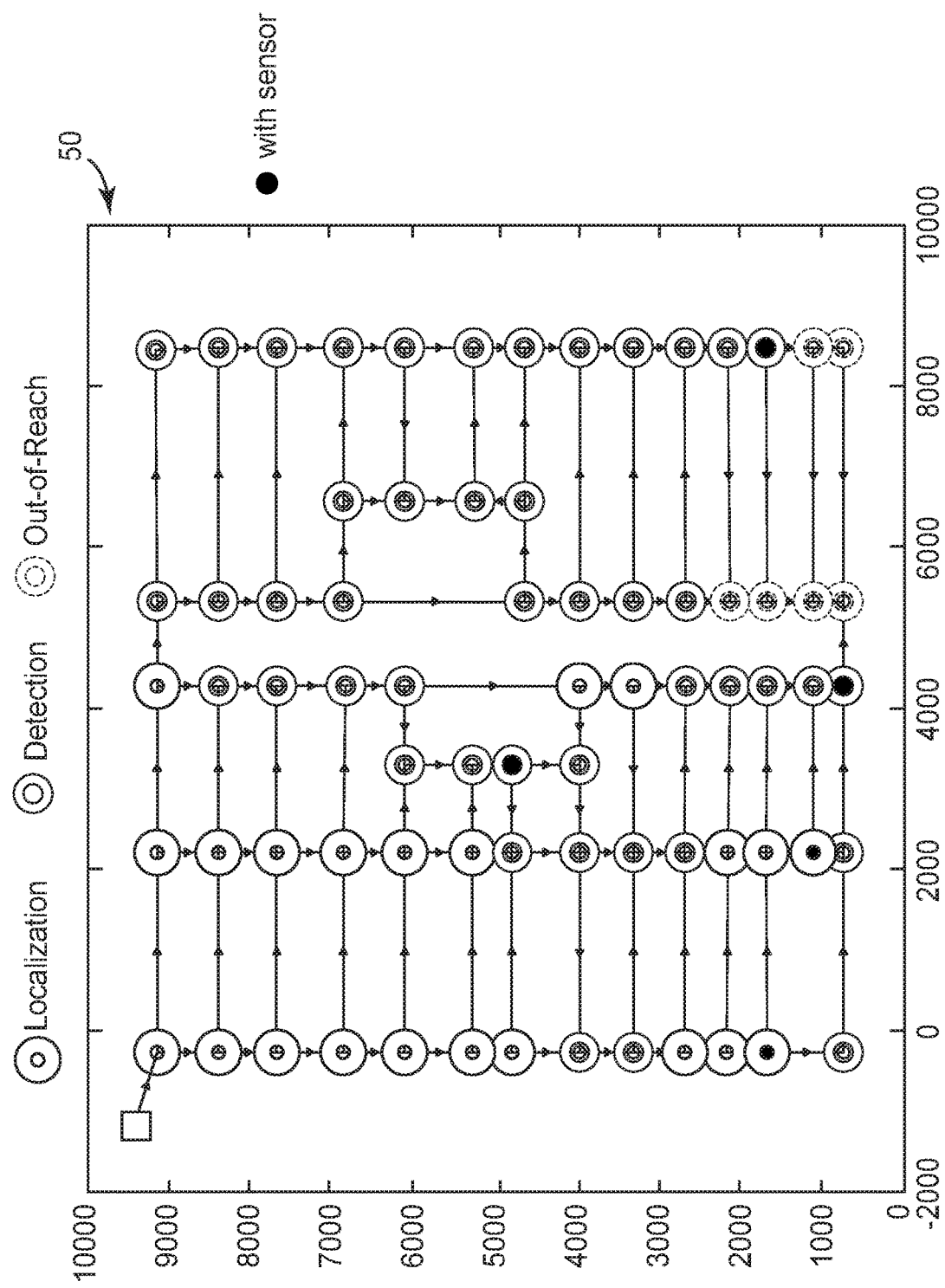

SYSTEMS AND METHODS FOR MODELING, ANALYZING, DETECTING, AND MONITORING FLUID NETWORKS

CROSS REFERENCE TO RELATED APPLICATIONS

This application is a national stage filing under 35 U.S.C. 371 of PCT/US2017/044722, filed Jul. 31, 2017, which claims the benefit of U.S. Application No. 62/381,944, filed Aug. 31, 2016, the disclosure of which is incorporated by reference in its/their entirety herein.

TECHNICAL FIELD

The present disclosure relates to methods and systems of modeling, analyzing, monitoring, and detecting fluid networks.

BACKGROUND

Fluid networks such as a water network may experience problems that impact availability and quality including slow or rapid leaks, corrosion of the transporting infrastructure, contamination, etc. Such problems may not be discovered and resolved until they have created a significant impact on infrastructure, water quality, or health. An example is the Elk River Chemical Spill on January, 2014 where about 300,000 residents were affected and 122 were hospitalized because of the contamination.

SUMMARY

There is a desire to enable early or real-time detection of problems (e.g., pipe-coating issues, leaks/cracks, contamination, etc.) in a fluid network, and enable a preemptive action, rather than reactive, by predicting when and where an issue/problem is likely to occur.

In one aspect, the present disclosure describes a method of optimally determining sensor or infrastructure placement in a fluid network. The method includes creating a model of the fluid network. The model includes i) a plurality of directionally connected nodes representing fluid infrastructure disposed in the fluid network, and ii) one or more sensors positioned at one or more selected locations in the fluid network. The method further includes representing the model as a matrix data structure associated with a processor disposed outside of the fluid network, analyzing, via the processor, the matrix to evaluate whether each node of the model satisfies one or more localizability criteria. Analyzing the matrix includes interpreting and executing a plurality of instructions associated with the processor. The sensor or infrastructure placement in the fluid network is determined.

In another aspect, the present disclosure describes a system including one or more sensors positioned at one or more selected locations in a fluid network. The sensors are configured to collect data from the fluid network at the respective locations. A processor is disposed outside of the fluid network. The processor is configured to receive the data from the sensors, and analyze the data based on a model of the fluid network. The model includes a plurality of directionally connected nodes representing fluid infrastructure disposed in the fluid network. A plurality of instructions associated with the processor are interpretable and executable by the processor to analyze the data and determine sensor placement within the fluid network.

In another aspect, the present disclosure describes a method of determining an anomaly of interest in a fluid network. The method includes providing one or more sensors disposed at one or more selected locations in the fluid network. The sensors are configured to collect data from the fluid network at the respective locations. The method further includes collecting, via the one or more sensors, data from the fluid network at the one or more locations, receiving, via a processor, the data from the sensors, and analyzing, via the processor, the data based on a model of the fluid network. The model is represented as a directed graph associated with the processor. The directed graph includes a plurality of directionally connected nodes where one or more imaginary nodes are added between two adjacent nodes.

In another aspect, the present disclosure describes a method of determining sensor coverage in a fluid network. The method includes creating a model of the fluid network. The model includes a plurality of directionally connected nodes representing fluid infrastructure disposed in the fluid network. The method further includes representing the model as a matrix data structure associated with a processor disposed outside of the fluid network, and analyzing, via the processor, the matrix to evaluate whether each node satisfies one or more localizability criteria. Analyzing the matrix includes interpreting and executing a plurality of instructions associated with the processor. The method further includes assigning each node to one of a localization area, a detection area, and an out-of-reach area.

Various unexpected results and advantages are obtained in exemplary embodiments of the disclosure. Such advantage of exemplary embodiments of the present disclosure include early or real-time detection and determination of problems/issues in a fluid network, preemptive actions including predicting possible issues/problems in the fluid network, optimal sensor or fluid infrastructure placement, etc.

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which:

FIG. 6D illustrates a diagram of a fluid network divided into a localization area, a detection area, and an out-of-reach area, according to another embodiment.

Figure 1:
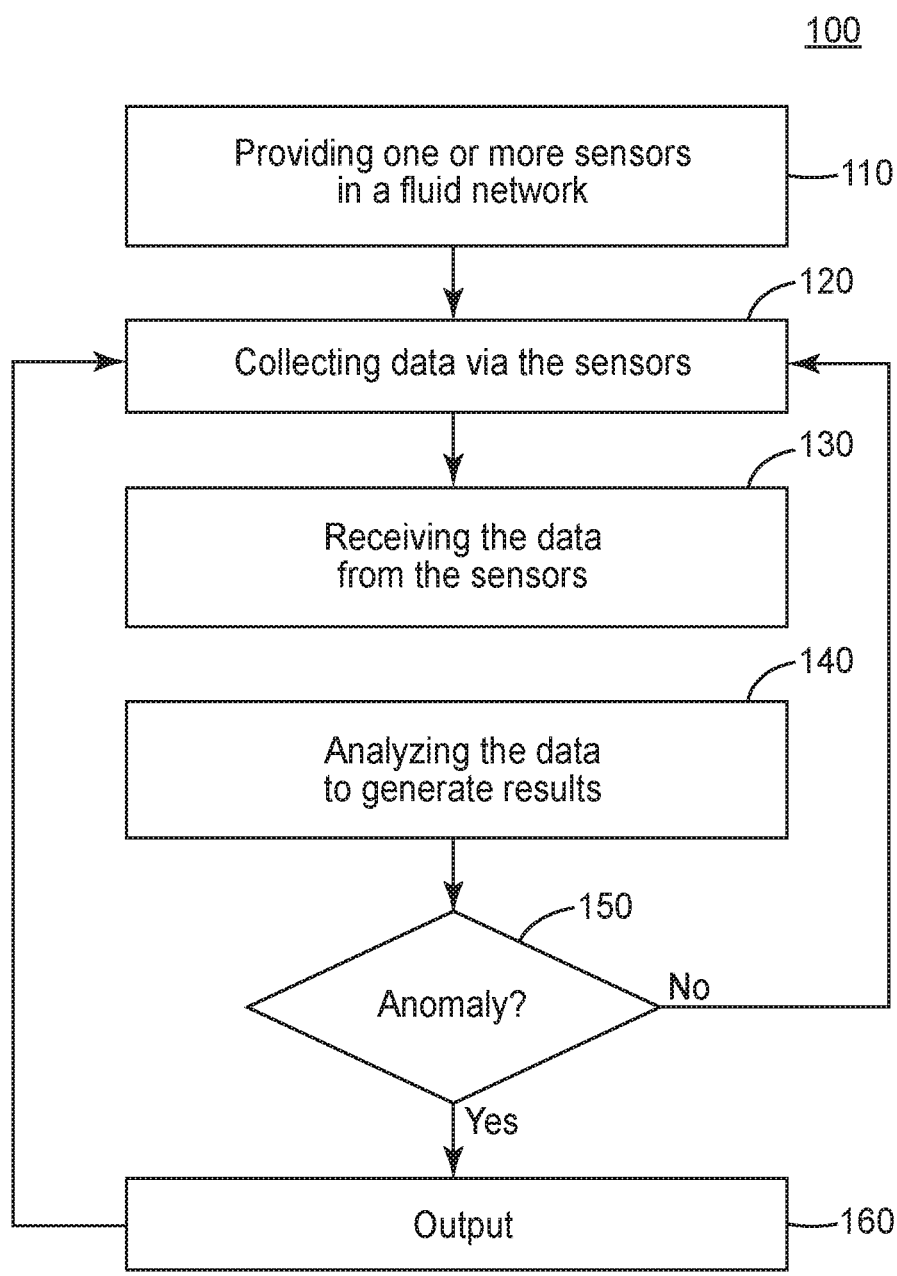
FIG. 1 is a flow diagram of a method of detecting an anomaly of interest in a fluid network, according to one embodiment.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

The present disclosure provides methods and systems to enable early or real-time detection of problems (e.g., pipe-coating issues, leaks, cracks, contaminations, etc.) in a fluid network, and enable preemptive actions including predicting when and where an issue/problem in a fluid network may be likely to occur. Fluid networks described herein may include a fluid distribution, treatment, and/or collection network such as, for example, a water pipeline distribution network, a water treatment system, a sewer system, a natural waterway such as rivers and tributaries, a gas line distribution network (e.g. methane or propane), oil pipeline distribution network, etc. Methods and systems described herein can solve the problem of difficult-to-detect problems in a fluid network, where slow leaks, corrosion of transporting infrastructure, or contamination issue may not be found until it has created a significant impact on infrastructure, water quality, or health.

FIG. 1 illustrates a flow diagram of a method 100 of monitoring anomaly of interest in a fluid network. At 110, one or more sensors are provided for the fluid network. The sensors can be any types of sensors capable of collecting data related to one or more parameters of the fluid network such as, for example, a disinfectant concentration, a contaminant concentration, a fluid pressure, a fluid flow rate, temperature, conductivity, a usage or predicted end-of-life of a filter, etc. An exemplary sensor includes the KAPTA™ 3000-AC4 from Endetec Veolia of Kingston, Canada. The sensors can be located at various locations inside a fluid network. For example, sensors can be provided to commercial water filters, residential areas (e.g., refrigerators), public places (e.g., water fountains), etc. The present disclosure provides methods on how to determine optimal sensor placement in the fluid network and methods on how to determine sensor coverage in the fluid network based on modeling the fluid network, which will be described further below. The method 100 then proceeds to 120.

At 120, the sensors are instructed by a processor to collect the data. The processor can be located in a remote computer (e.g., server or the Cloud) out of the fluid network. In some embodiments, sensors may be provided for filters distributed in the fluid network, and data collected by the sensor may indicate status of the respective filters. In some embodiments, each sensor can be instructed to collect data at an initial time, which can be stored in a database as initial values. The method 100 then proceeds to 130.

At 130, the collected data are transferred from the sensors and received by the processor. The data can be transmitted directly or indirectly via suitable technologies such as, for example, Wi-Fi, Bluetooth, Bluetooth Low Energy (BLE), cellular, Ethernet, etc. The collected data can be transferred in real time from the sensors, or be transferred at a later date to provide a retrospective indication of the fluid network. Data can also be collected at regular time intervals or an adapted time schedule based on a contextual situation. For example, data can be collected or transferred at a relatively higher frequency after a storm that may have damaged the fluid network, or when the filters are predicted to be near end-of-life. The method 100 then proceeds to 140.

At 140, the received data are analyzed by the processor to generate results. In some embodiments, the received data can be analyzed based on a model of the fluid network. In some embodiments, a model of fluid network can include directionally connected nodes representing fluid infrastructure disposed in the fluid network. The nodes can be ordered as a partially order set, where order of nodes may change depending on directions of fluid flow between nodes. For example, fluid flow direction may change where there are fluctuations in "usage" at some of the nodes. The model can be representation(s) of the fluid network including, for example, a directed acrylic diagraph (DAG). The representations of the fluid network (e.g., a directed acrylic diagraph) can be stored or processed by the processor as a matrix data structure such as, for example, an adjacency matrix, a reachability matrix, etc.

In some embodiments, historical data or other data related to the fluid network can be combined with the received real-time data from the sensors and analyzed by the processor. Such other types of data may include, for example, previous issues/problems in the fluid network (e.g., breakage, replacement, etc.), weather (thunderstorms, floods, etc., that might be the cause of a damage on the fluid network in certain areas), temperature, pressure, or conductivity variations, and reported damage (e.g., fallen tree, electrical lines, and its correlation with fluid network damage). In some embodiments, baseline measurements can be conducted to determine whether there is any initial contamination such as contamination introduced during installation of fluid infrastructure. In some embodiments, historical data from the sensors related to the fluid network can be analyzed in terms of time, geography, etc., to derive an anomalous pattern. The data can be stored in, for example, a database associated with the processor or in a Cloud. The generated results including, for example, analysis reports, alerts, alarms, etc. The method 100 then proceeds to 150.

At 150, based on the analysis of the data, it is determined, via the processor or an operator/user, whether there is anomaly of interest in the fluid network. Possible anomalies of interest may include, for example, a contamination, an infrastructure fault, fluid leak, elevation or declination of temperature, pressure, or conductivity, or combinations thereof, etc. In some embodiments, the processor may further determine possible locations of the anomaly inside the fluid network. When there is an anomaly in the fluid network, the method 100 proceeds to 160 to generate an output in the form of, for example, an alarm, an alert, a report, etc. When there is no anomaly in the fluid network, the method 100 proceeds back to 120. In some embodiments, the output may include prediction of future fluid network problems/issues such as, for example, pipe failures based on similar environments by classifying the fluid network based on age, size, usage, etc. In some embodiments, the output may include whether someone is stealing resources from the fluid network via a noticeable difference in network characteristics (e.g., a new "node" in the model being detected). In some embodiments, the output may be used to provide prioritization of water sourcing, shutdown, and/or diversion based on the infrastructure it is serving. For example, if a contamination is detected, rerouting of clean water can be prioritized to a hospital over other infrastructure. In some embodiments, the output may be provided to homeowners by comparing their filter usage to their neighbors (e.g., to determine whether a water health issue is localized to the house).

Figure 2:
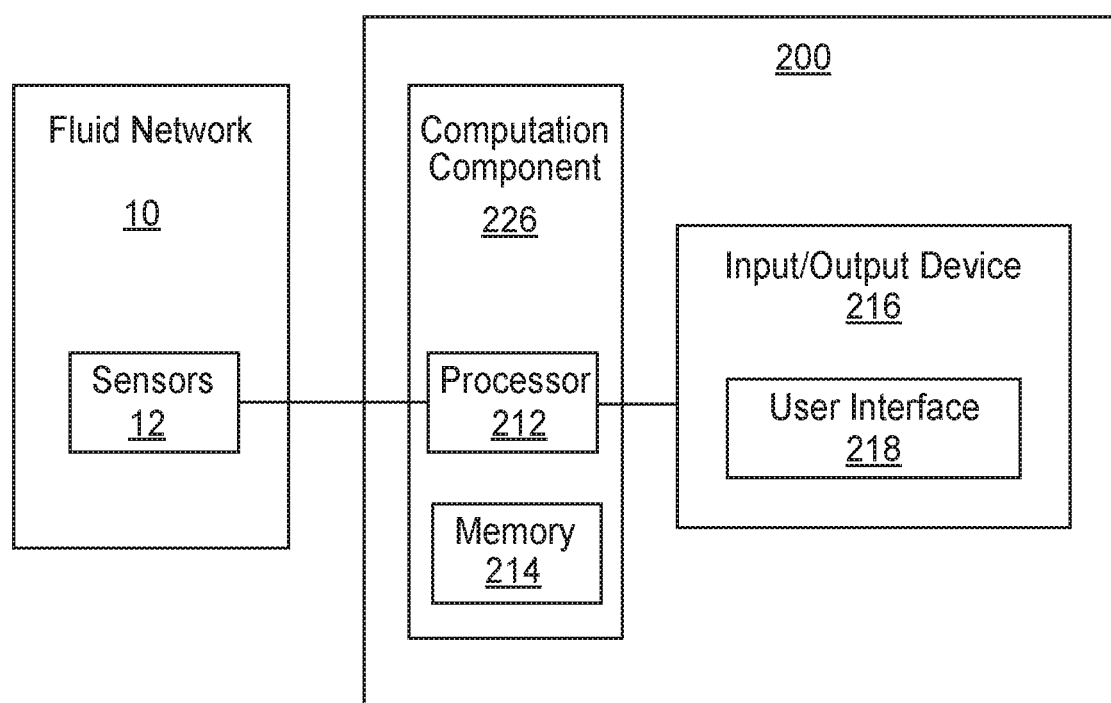
FIG. 2 illustrates a block diagram of a system for detecting an anomaly of interest in a fluid network, according to one embodiment.

FIG. 2 illustrates a detection system 200 for determining an anomaly of interest in a fluid network 10 by implementing, for example, the method 100, according to one embodiment. The fluid network 10 can include a fluid distribution, treatment, and/or collection network such as, for example, a water pipeline distribution network, a water treatment system, a water collection network, a sewer system, natural waterways such as rivers and tributaries, a gas line distribution network (e.g. methane or propane), oil pipeline distribution network, etc. One or more sensors 12 are provided for various locations inside the fluid network 10.

The detection system 200 includes the sensors 12, a computation component 226, and one or more input/output devices 216. The sensors 12 can be any types of sensors capable of collecting data related to one or more parameters of the fluid network such as, for example, a disinfectant concentration, a contaminant concentration, a fluid pressure, a fluid flow rate, temperature, conductivity, a usage or predicted end-of-life of a filter, etc. Exemplary sensors may include passive, wireless sensors. The sensors 12 may include a radio-frequency identification (RFID), which can identify individual fluid infrastructure (e.g., filter) and its related information (e.g., size, model, usage, time of installation, status, etc.).

In some embodiments, the fluid network 10 may be a water network provided with a water filter system including water filters and/or other water filtration, separation and/or purification products. The water filter system is applied to reduce contaminates such as, for example, chlorine and/or chloramine, particulates, lead, etc. The sensors 12 can be provided for the water filters to track the usage/end-of-life of the water filters.

In the embodiment of FIG. 2, the computation component 226 includes a processor 212 and a memory 214. The computation component 226 is functionally connected to the sensors 12, receives signals or data related to the fluid network 10 from the sensors 12, and analyze the received signals/data to generate results including, for example, analysis reports, alerts, alarms, etc. In some embodiments, the data received from the sensors 12 can be stored in the memory 214. In some embodiments, a model can be created to represent the fluid network 10. The model may include directionally connected nodes representing fluid infrastructure of the fluid network. The model can include, for example, a directed graph or a partially ordered set, which is stored in the memory 214 as data in the form of an adjacency matrix. The processor 212 can analyze the model by interpreting and executing instructions from a software program associated with the processor 212.

The memory 214 stores information. In some embodiments, the memory 214 can store instructions for performing the methods or processes described herein. In some embodiments, data related to the fluid network, or the model of the fluid network can be pre-stored in the memory 214.

The memory 214 may include any volatile or non-volatile storage elements. Examples may include random access memory (RAM) such as synchronous dynamic random access memory (SDRAM), read-only memory (ROM), non-volatile random access memory (NVRAM), electrically erasable programmable read-only memory (EEPROM), and FLASH memory. Examples may also include hard-disk, magnetic tape, a magnetic or optical data storage media, a compact disk (CD), a digital versatile disk (DVD), a Blu-ray disk, and a holographic data storage media. Data may also be stored in a Cloud computing environment.

The processor 212 may include, for example, one or more general-purpose microprocessors, specially designed processors, application specific integrated circuits (ASIC), field programmable gate arrays (FPGA), a collection of discrete logic, and/or any type of processing device capable of executing the techniques described herein. In some embodiments, the processor 212 (or any other processors described herein) may be described as a computing device. In some embodiments, the memory 214 may be configured to store program instructions (e.g., software instructions) that are executed by the processor 212 to carry out the processes or methods described herein. In other embodiments, the processes or methods described herein may be executed by specifically programmed circuitry of the processor 212. In some embodiments, the processor 212 may thus be configured to execute the techniques for analyzing data related to a fluid network described herein. The processor 212 (or any other processors described herein) may include one or more processors.

Input/output device 216 may include one or more devices configured to input or output information from or to a user or other device. In some embodiments, the input/output device 216 may present a user interface 218 where a user may control the assessment of a fluid network. For example, user interface 218 may include a display screen for presenting visual information to a user. In some embodiments, the display screen includes a touch sensitive display. In some embodiments, a user interface 218 may include one or more different types of devices for presenting information to a user. The user interface 218 may include, for example, any number of visual (e.g., display devices, lights, etc.), audible (e.g., one or more speakers), and/or tactile (e.g., keyboards, touch screens, or mice) feedback devices. In some embodiments, the input/output devices 216 may represent one or more of a display screen (e.g., a liquid crystal display or light emitting diode display) and/or a printer (e.g., a printing device or component for outputting instructions to a printing device). In some embodiments, the input/output device 116 may be configured to accept or receive program instructions (e.g., software instructions) that are executed by the processor 112 to carry out the embodiments described herein.

The detection system 200 may also include other components and the functions of any of the illustrated components including the processor 212, the memory 214, and the input/output devices 216 may be distributed across multiple components and separate devices such as, for example, computers. The detection system 200 may be configured as a workstation, desktop computing device, notebook computer, tablet computer, mobile computing device, or any other suitable computing device or collection of computing devices. The detection system 200 may operate on a local network or be hosted in a Cloud computing environment. The illustrated components of FIG. 2 are shown merely to explain various aspects of the present disclosure and the addition or removal of components would be apparent to one of skill in the art.

The detection system 200 allows a user to determine anomalies in a fluid network in real time. In some embodiments, the collected data from a fluid network can be automatically analyzed in real time, via the processor, based on a model of the fluid network to generate results for output. The detection system 200 further allows a user to predict possible issues/problems that a fluid network may have in the future.

Figure 3A:
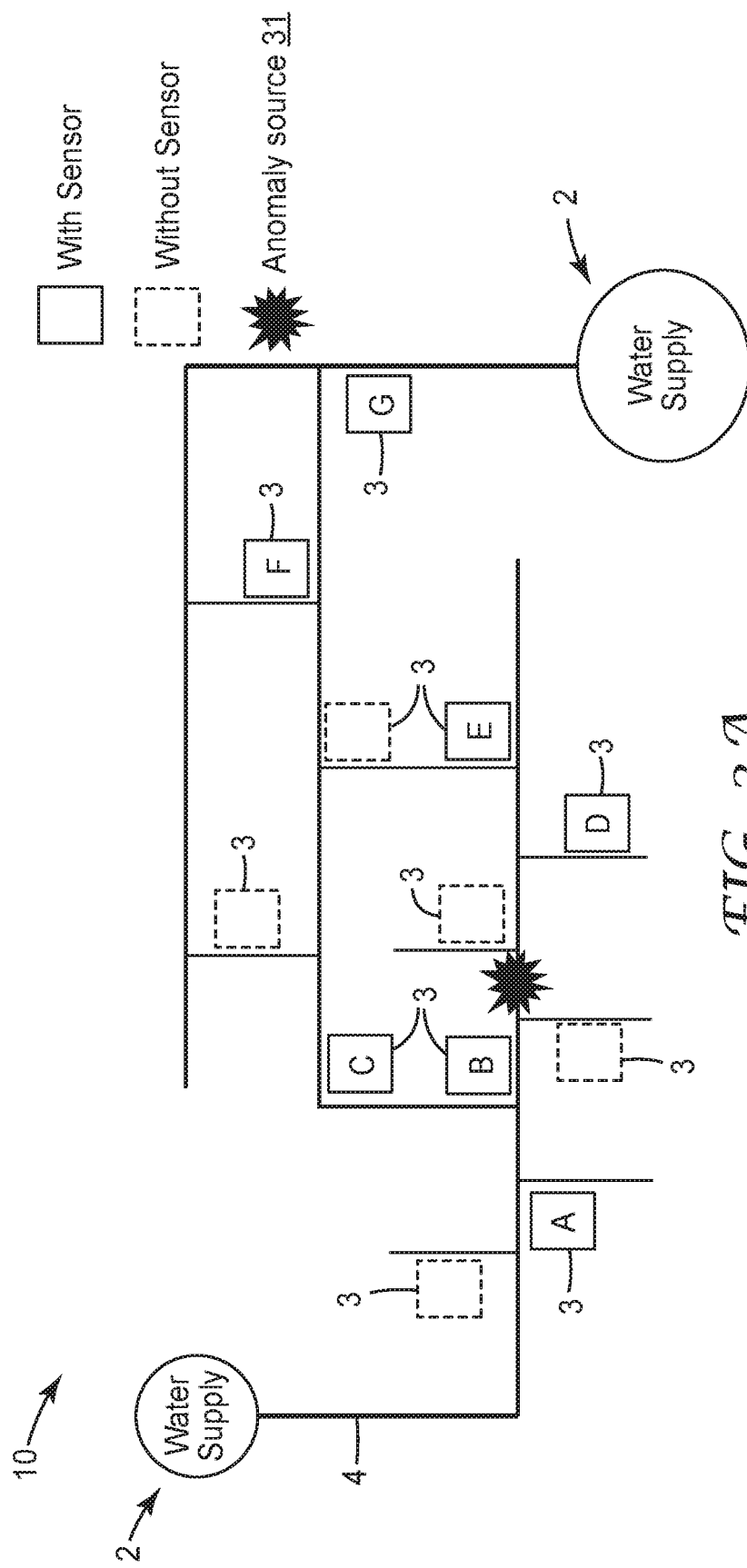
FIG. 3A illustrates a schematic diagram of a fluid network provided with sensors, according to one embodiment.

FIG. 3A illustrates a diagram of a water pipeline network 10 as an exemplary fluid network, according to one embodiment. Water is supplied from water supply 2. Various fluid infrastructures 3 are connected by water pipelines 4. Sensors are provided at selected locations A through G in the water pipeline network 10. The sensors can be functionally connected to a processor of a detection system such as the detection system 200 of FIG. 2, and configured to collect data at the various locations in the network 10, which can then be transmitted to the processor of the detection system to analyze. Based on the sensor data received from the locations A-G, the processor of the detection system can analyze the data and determine that the locations A-C, F and G have "good" water condition, while the locations D and E have "bad" water condition in the illustrated example. The processor can further determine, based on a model of the network 10, that the possible cause of anomaly (e.g., burst/contamination) may be located at location 31 in the network 10 between the locations B and D.

Figure 3B:
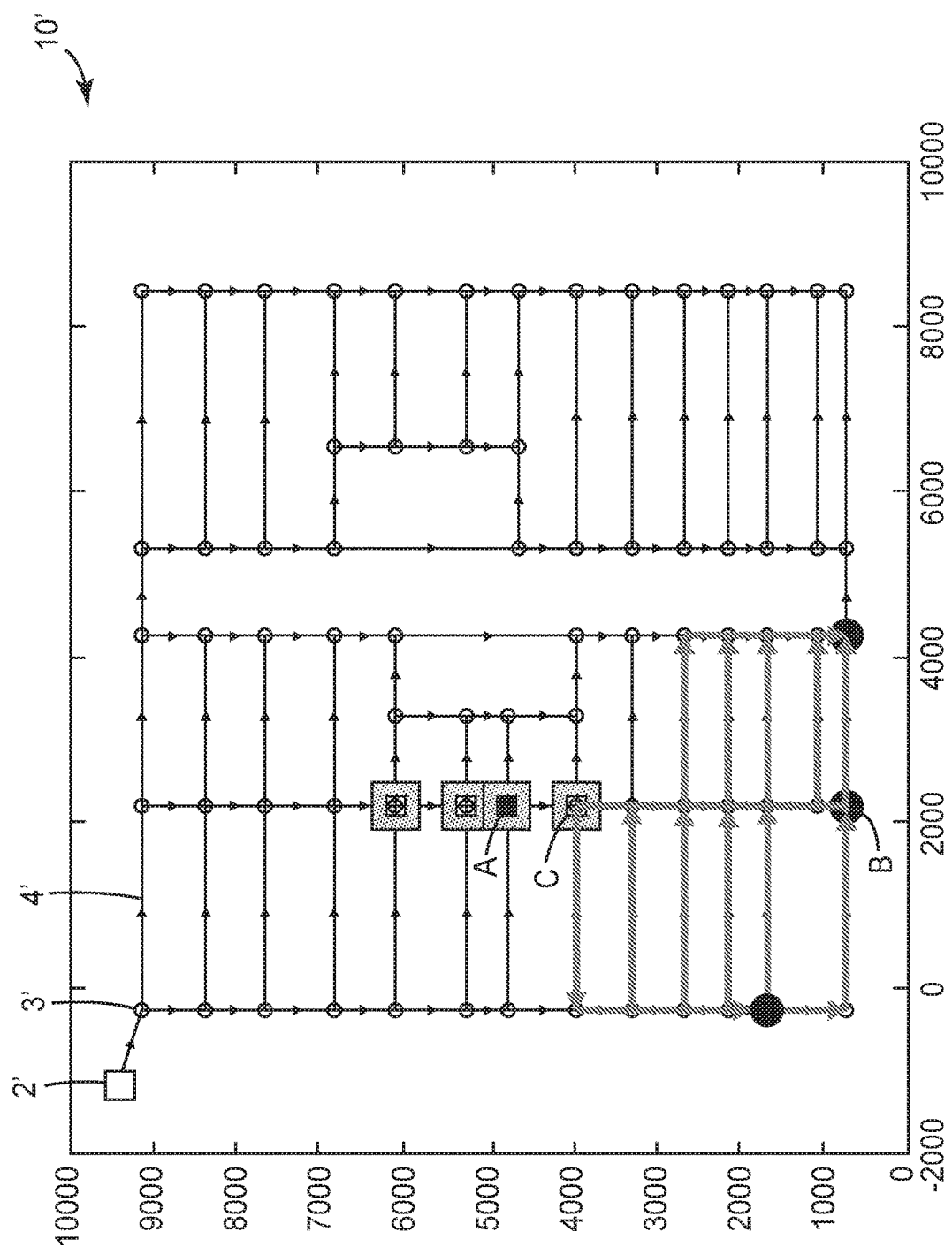
FIG. 3B illustrates a schematic diagram of a fluid network provided with sensors, according to another embodiment.
Figure 3B:
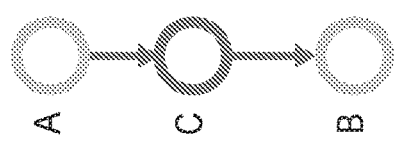

FIG. 3B illustrates a diagram of a water pipeline network 10' as another exemplary fluid network. Water is supplied from a water supply 2' to the water pipeline network 10'. Various fluid infrastructures 3' are connected by water pipelines 4'. The various fluid infrastructures 3' can be represented by nodes that are directionally connected where arrows correspond to fluid flow directions in the fluid network. As an example, fluid infrastructure located at nodes A, B and C are directionally connected as shown in the left inset, where node C is a dependency-connection between node A and node B, and nodes A and B are therefore not dependency (d)-separated. Node C is defined as a d-separator in the path from node A to node B.

In the present disclosure, models are created to represent various fluid networks. A model of fluid network can include directionally connected nodes representing the fluid infrastructure disposed in the fluid network. Properties of fluid flow such as, e.g., flow directions, flow rate, within the fluid network can be measured by flow sensors or derived using fluid dynamics based on factors such as, for example, pipe sizes, length, etc. In some embodiments, a model can be representation(s) of the fluid network including, for example, a directed acrylic diagraph (DAG). The representations of the fluid network (e.g., a directed acrylic diagraph) can be stored or processed by a processor as a matrix data structure matrix such as, for example, an adjacency matrix, a reachability matrix, etc.

Figure 4A:
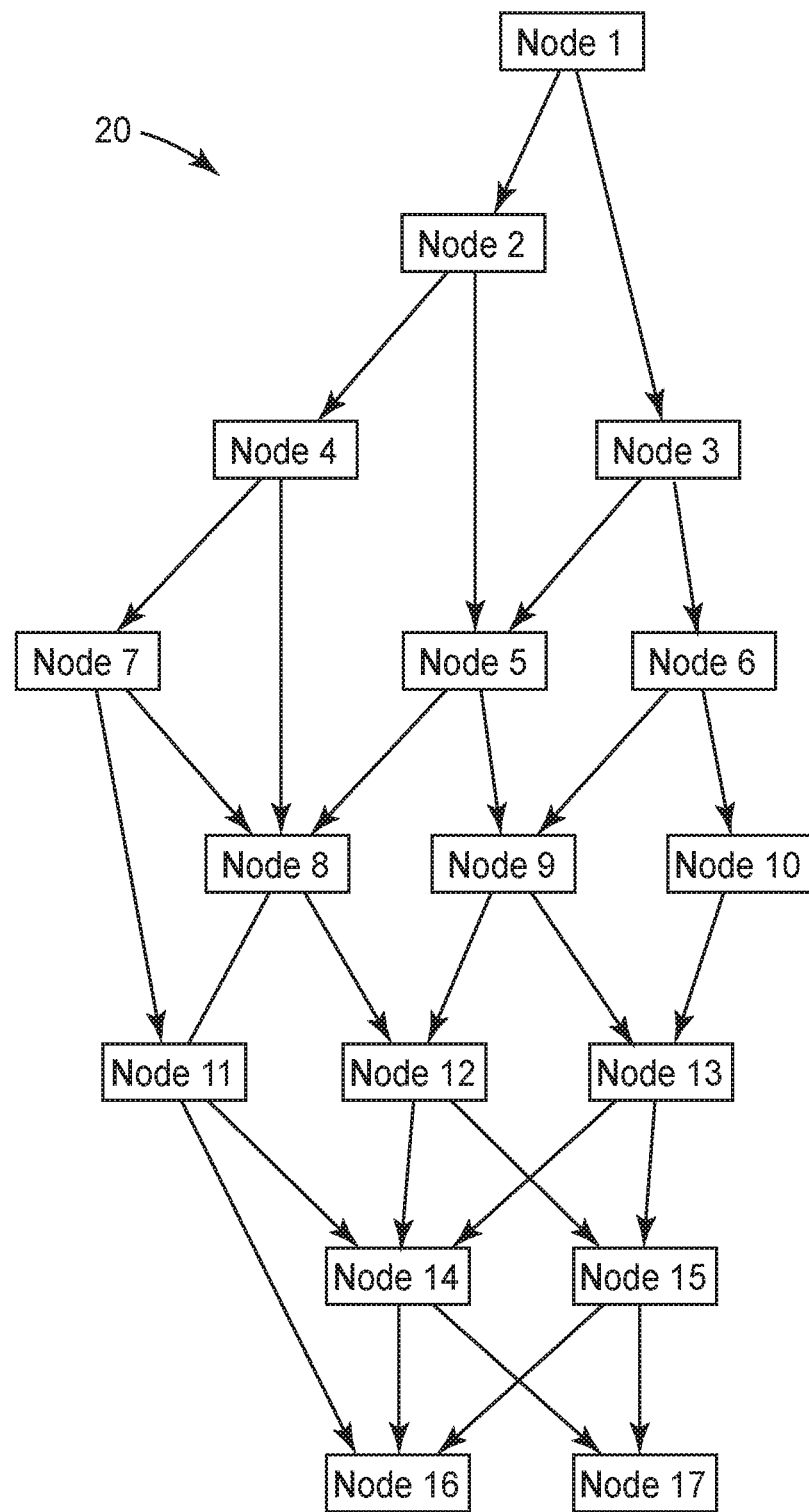
FIG. 4A illustrates a directed graph representing a fluid network, according to one embodiment.

FIG. 4A illustrate a model 20 of a fluid network, according to one embodiment. In the model 20, various fluid infrastructure are represented by nodes 1 through 17. For example, node 1 may represent a water supply. Nodes 1-17 are directionally connected to form a directed graph, which is a partially ordered set. The arrows in FIG. 4A correspond to fluid flow directions in the fluid network. It is to be understood that a fluid network can be represented by various directed graphs. A directed graph of a fluid network can further be represented by a matrix data structure such as, for example, an adjacency matrix, reachability matrix, etc. The matrix data structure can be stored and/or analyzed by a processor.

The present disclosure provides methods to analyze, via a processor such as processor 212 of FIG. 2, a model of fluid network. In some embodiments, the model or representations of the model can be analyzed to evaluate whether a node or a set of nodes satisfies one or more localizability criteria. In some embodiments, the localizability criteria may include, for example, for a given node or node set, evaluating whether there are at least two sensors disposed downstream of the given node or node set which have the respective paths not sharing any d-separator with respect to the given node or node set. When a given node satisfies the localizability criteria, no sensor is provided to the given node. When the given node does not satisfy the localizability criteria, one or more sensors are provided to the given node. Instructions associated with the processor can be interpreted and executed to analyze the model or representations of the model. The above process of analyzing may include dynamic programming including a bottom-up approach starting from the lowest level in the representations of the model, as further explained by one embodiment as shown in FIG. 4B.

Figure 4B:
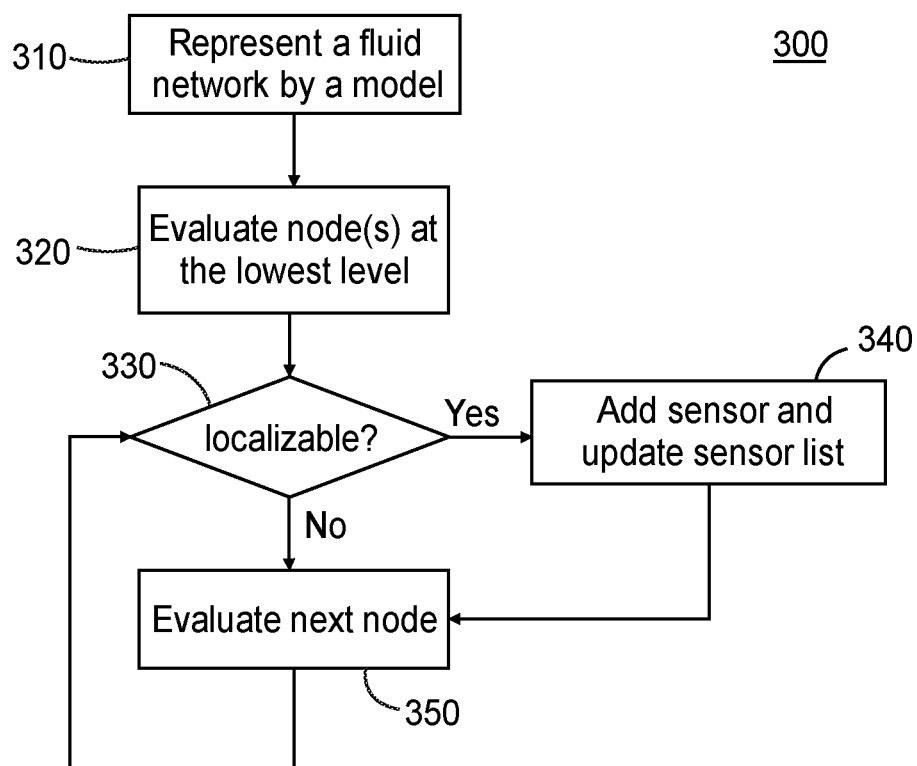
FIG. 4B is a flow diagram of a method of optimally determining sensor placement in a fluid network, according to one embodiment.

FIG. 4B is a flow diagram of a method 300 for optimally determining sensor placement in a fluid network, according to one embodiment. At 310, a fluid network is represented by a model. The model can be, for example, a directed graph such as the directed graph 20 shown in FIG. 4A. The directed graph can be a partial order set where nodes are ordered in different levels. The method 300 then proceeds to 320. At 320, one or more nodes or node sets at the lowest level of the model are evaluated to determine at 330 whether the node or node set satisfies localizability criteria, e.g., whether there are at least two sensors disposed downstream of the given node or node set which have the respective paths not sharing any d-separator with respect to the given node or node set. When the node or node set satisfies the localization criteria, the method 300 proceeds to 340. When the node or node set does not satisfy the localizability criteria, the method 300 proceeds to 350. At 340, sensor(s) is added to the node or node set, and the model (e.g., directed graph) is updated with the added sensor(s). At 350, next mode or mode set at the same level or an upper level is evaluated in the same manner. The process continues until the node(s) at the upper most level of the fluid network is evaluated.

Figure 4C:
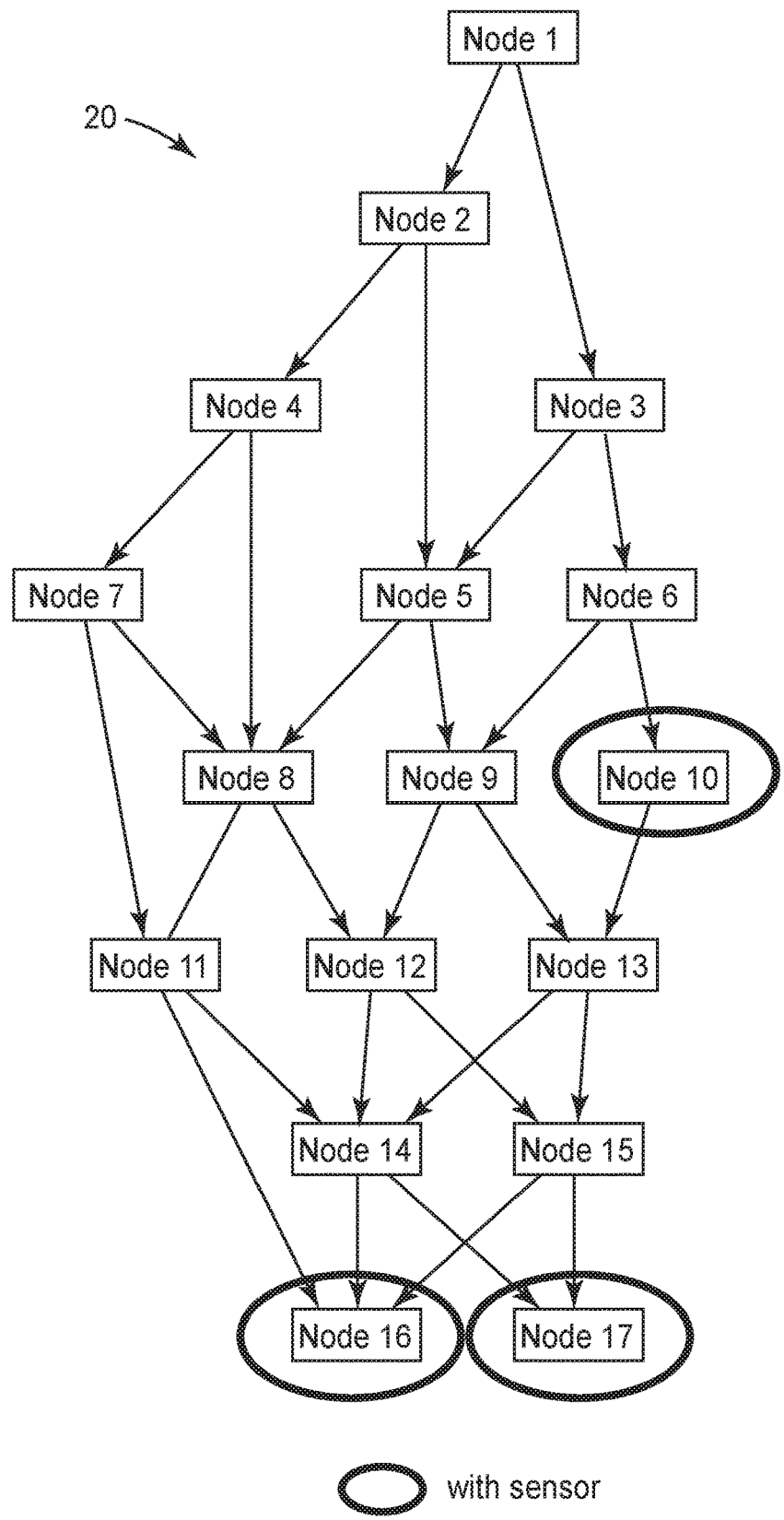
FIG. 4C illustrates the directed graph of FIG. 4A provided with sensors at selected locations, according to one embodiment.
Figure 4D:
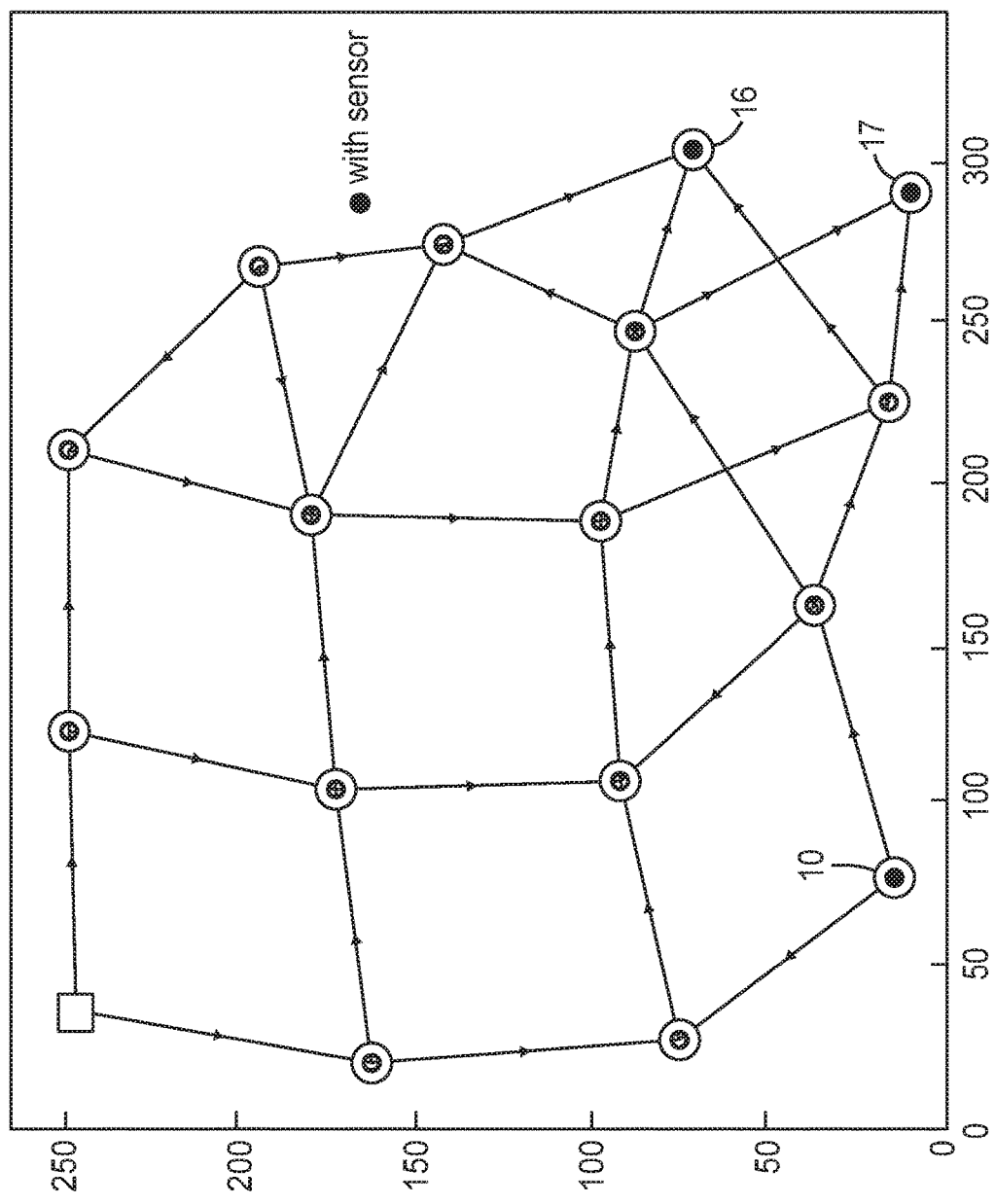
FIG. 4D illustrates a reformatted version of the directed graph of FIG. 4C provided with sensors at selected locations.

Application of the method 300 of FIG. 4B to the fluid network represented by the model 20 of FIG. 4A produces results that are shown in FIGS. 4C-D. The evaluation starts from the lowest level, e.g., node 16 or 17 in the directed graph 20. It is found that nodes 16 and 17 do not satisfy the localizability criteria. There are no sensors downstream of node 16 or 17. Sensors are added at nodes 16 and 17, respectively, and the directed graph 20 is updated with the added sensors at nodes 16 and 17. Then, node 14 or 15 at the next level can be evaluated. It is found that nodes 14 and 15 satisfy the localizability criteria. There are two sensors downstream at nodes 16 and 17, and the respective paths from nodes 14 and 15 to the two sensors at nodes 16 and 17 do not sharing any d-separator. No sensors will be provided to nodes 14 and 15. This bottom-up approach continues and each node can be evaluated. It is found that nodes 11-13, 8, 9, and 1-7 satisfy the criteria and no sensors will be provided to these nodes. Node 10 does not satisfy the localizability criteria. The respective paths from node 10 to the two sensors at nodes 16 and 17, e.g., 10-13-14-16 and 10-13-15-17, can share a d-separator (e.g., node 13). A sensor is provided to node 10 and the directed graph 20 is updated.

With sensors being placed at nodes 16, 17 and 10, it is sufficient to cover the whole fluid network. That is, by analyzing the data from the sensors located at nodes 10, 16 and 17, a processor of a detection system can explicitly determine the status at each nodes in the fluid network. FIG. 4D illustrates a reformatted version of the directed graph of FIG. 4C provided with sensors at selected locations. In some embodiments, when there is an anomaly in the fluid network, the processor can explicitly determine the location of anomaly by analyzing the sensor data. For example, when sensors data indicate that nodes 11, 14 and 16 have contamination and the remaining nodes have no contamination, the processor can determine that the cause of contamination is located at node 11.

When a fluid network requires n sensors to completely cover the fluid network, a complexity index of the network can be expressed as the ratio of the required number n of sensors and the number of nodes in the fluid network. For example, the complexity index of the fluid network 20 of FIG. 4A is 3/17.

It is to be understood that in some embodiments, one or more nodes of a model can be grouped into respective node sets before evaluation. For example, nodes 14 and 15 of FIG. 4A can be grouped into a single node set which can be evaluated. Each node set can include one or more adjacent nodes, and each node set can be evaluated, in the same manner as shown in FIGS. 4B-C, to determine whether the node sets or a combination of nodes and node sets satisfy the localizability criteria.

Figure 5A:
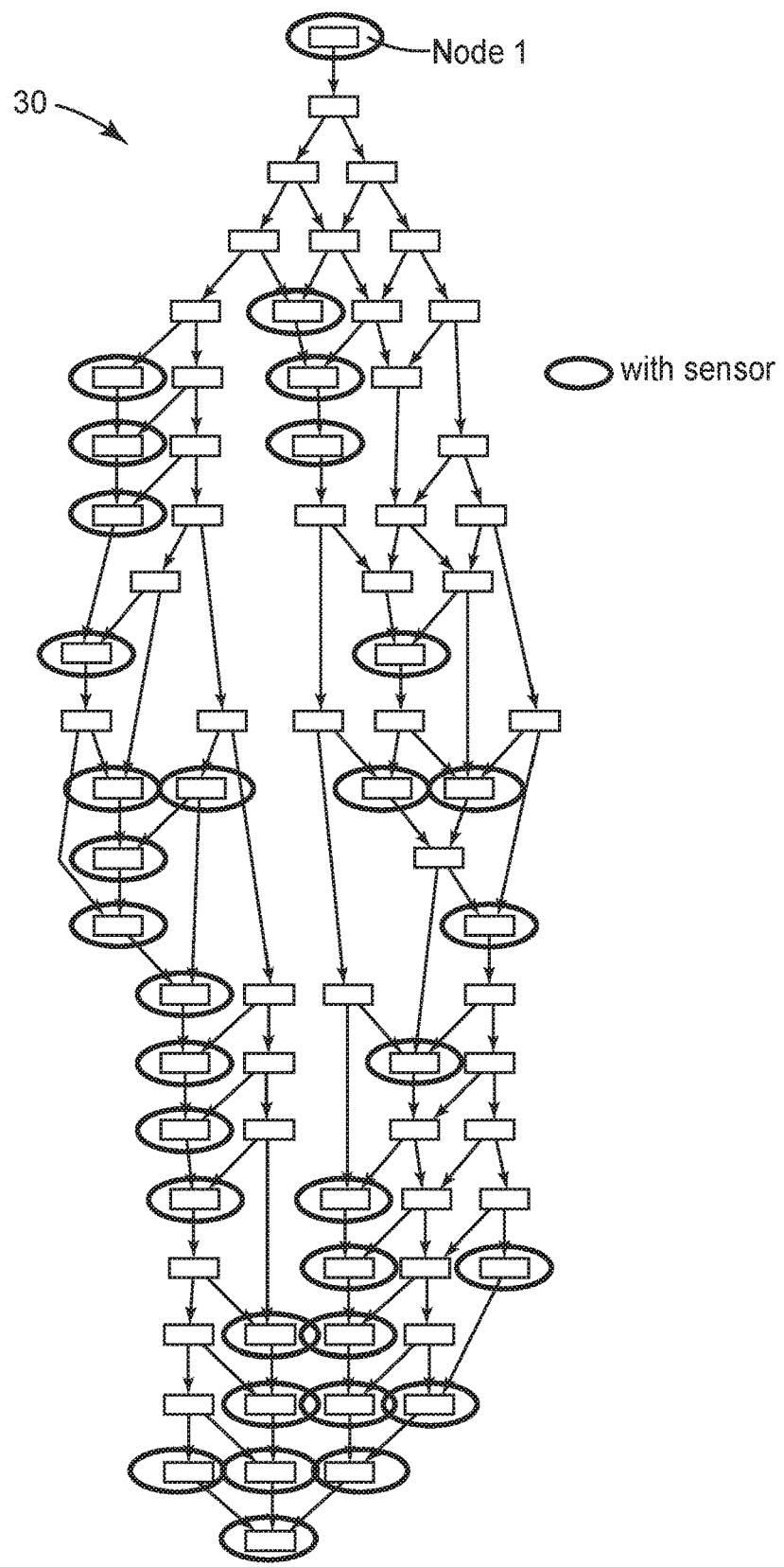
FIG. 5A illustrates a directed graph representing a fluid network with placement of sensors at selected locations, according to one embodiment.
Figure 5B:
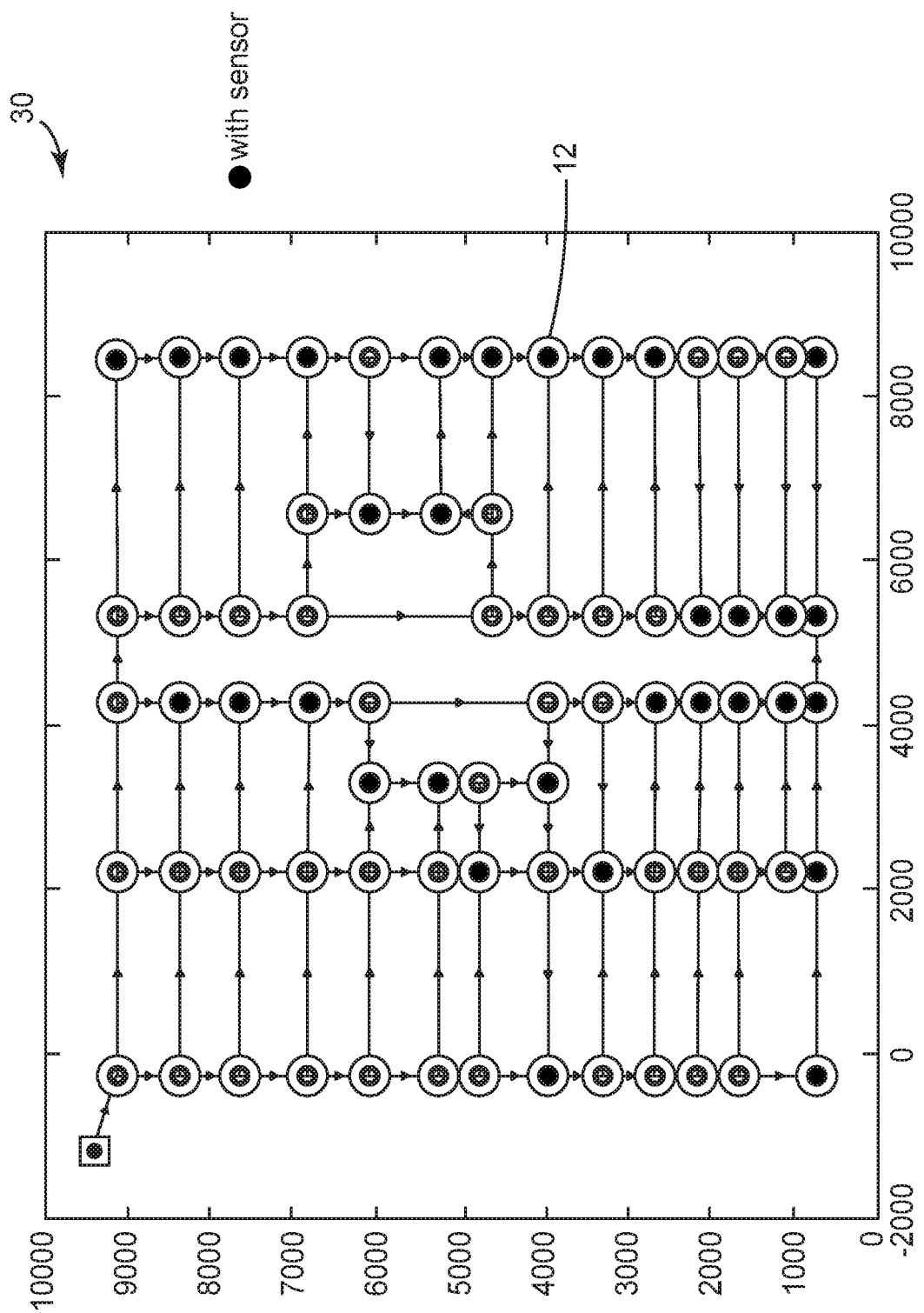
FIG. 5B illustrates a reformatted version of the directed graph of FIG. 5A.

FIG. 5A illustrate a model 30 of a fluid network, according to another embodiment. The fluid network is represented by a directed graph. Node 1 may represent a water supply. The model 30 can be analyzed in a manner similar as shown in FIGS. 4A-D for the model 20, as discussed above. The model 30 includes 74 nodes among which thirty-two nodes do not satisfy the localizability criteria and sensors are provided for the thirty-two nodes (e.g., circled nodes in FIG. 5A) to completely cover the whole fluid network 30. The complexity index of the fluid network 30 of FIG. 5A is 32/74. FIG. 5B illustrates a reformatted version of the directed graph of FIG. 5A provided with sensors at selected locations.

Figure 5C:
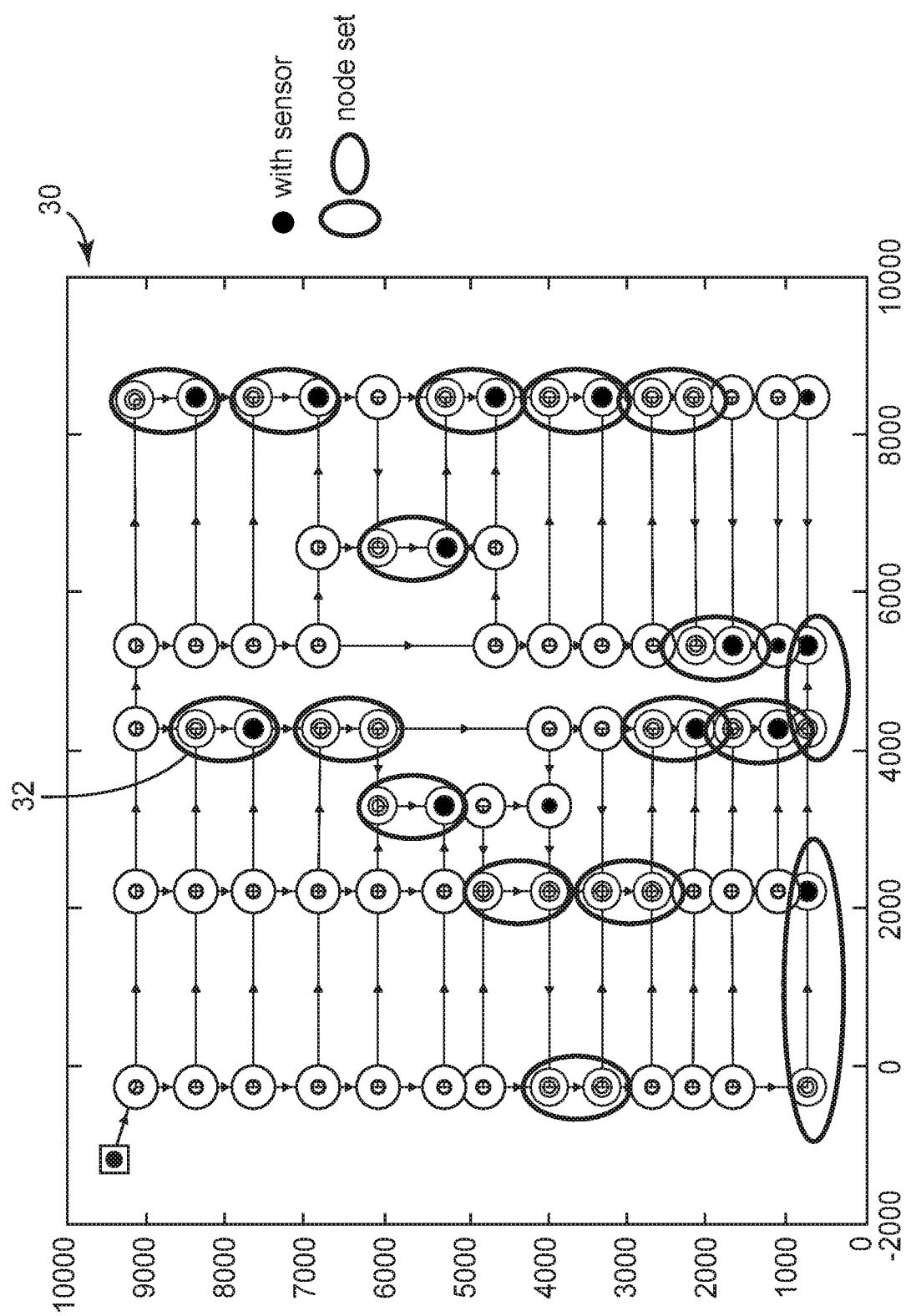
FIG. 5C illustrates grouping adjacent nodes into node sets in the model of FIG. 5B, according to one embodiment.

In some embodiments, the nodes of the model 30 can be first grouped into respective node sets before evaluation. FIG. 5C shows that some adjacent nodes are grouped into the same node set 32 (e.g., within the same circle). In this manner, the number of required sensors to completely cover the whole fluid network can decrease from 32 to 15, as compared to FIG. 5B. The tradeoff is that when one specific node set is determined to be the cause of an anomaly, it may not tell the explicit location (e.g., which node) of anomaly within the specific node set.

Figure 5D:
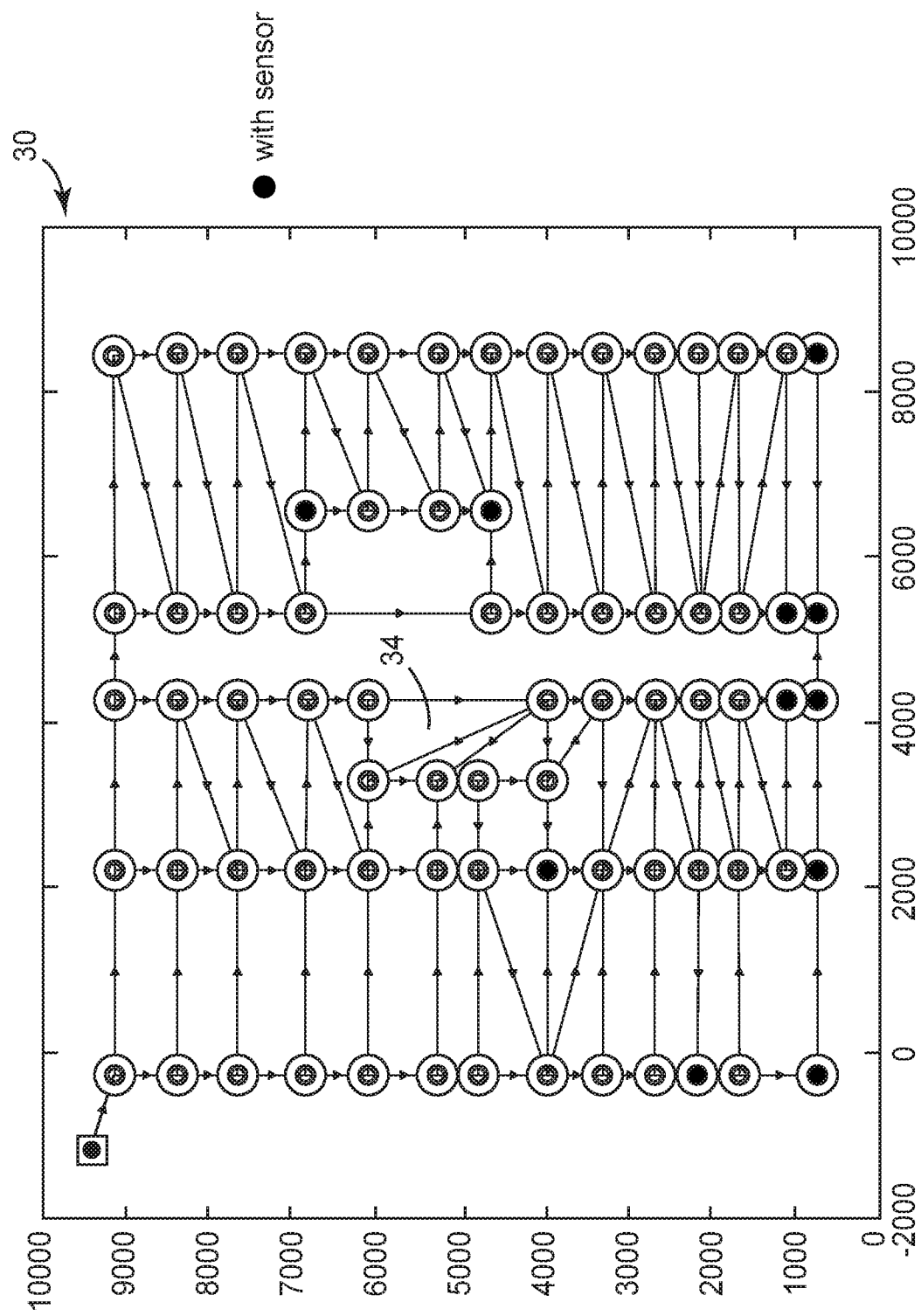
FIG. 5D illustrates a modification of the fluid network of FIG. 5B by adding fluid paths, according to one embodiment.

In some embodiments, a fluid network can be modified to reduce the number of sensors required for full coverage of the fluid network. As shown in FIG. 5D, one or more fluid connections 34 (e.g., pipelines) can be added to directionally, fluidly connect fluid infrastructure represented by nodes. When the fluid connections 34 are added in FIG. 5D, the number of required sensors to completely cover the whole fluid network can decrease from 32 to 11, as compared to FIG. 5B.

The present disclosure further provides methods of determining sensor coverage in a fluid network. The methods can include building a model of the fluid network. The model can include directionally connected nodes representing fluid infrastructure disposed in the fluid network. One or more sensors can be positioned at one or more selected locations in the fluid network. The model or representations of the model can be stored in, for example, a processor. The model or its representation can be analyzed, via the processor, to evaluate whether each node satisfies one or more localizability criteria. The localizability criteria may include, for example, for a given node, evaluating whether there are at least two sensors downstream of the given node which have the respective paths not sharing any d-separator with respect to the given node.

Based on results of the evaluation, the nodes of the model can be assigned to one of a localization area, a detection area, and an out-of-reach area. A localization area refers to an area in a fluid network where the location of anomaly (e.g., at a specific node) can be explicitly determined. A detection area refers to an area in a fluid network where data/signal related to an anomaly may be detected, but the exact location of the anomaly is unknown. An out-of-reach area refers to an area in the fluid network where no information related to the anomaly can be obtained. When a given node satisfies the localizability criteria, the given node is assigned to the localization area, and when the given node does not satisfy the localizability criteria, the given node is assigned to the detection area or the out-of-reach area.

When the given node does not satisfy the localizability criteria, the given node can be further evaluated to determine whether a sensor is located at or downstream from the given node. If no sensors are located at or downstream, the area corresponding to the given node is assigned to the out-of-reach area, otherwise it is assigned to the detection area.

In some embodiments, evaluation of paths between the given node and other nodes can be performed by using suitable algorisms regarding reachability of such as an advanced Markov chain method. An exemplary Markov chain method was described in Golnari et al., "Pivotality of Nodes in Reachability Problems Using Avoidance and Transit Hitting Time Metrics," 7th Annual Workshop on Simplifying Complex Networks for Practitioners SIMPLEX 2015, May 2015. It is to be understood the evaluation of paths can be performed by any other suitable algorithms.

In some embodiments, the sensitivity of sensors (e.g., sensitivity on measuring contamination concentration or its change) and an absorption probability matrix Q can be analyzed to determine a minimum detectable concentration of contamination level for at least some of the nodes. The absorption probability matrix Q of a fluid network will be described further below.

Figure 6A:
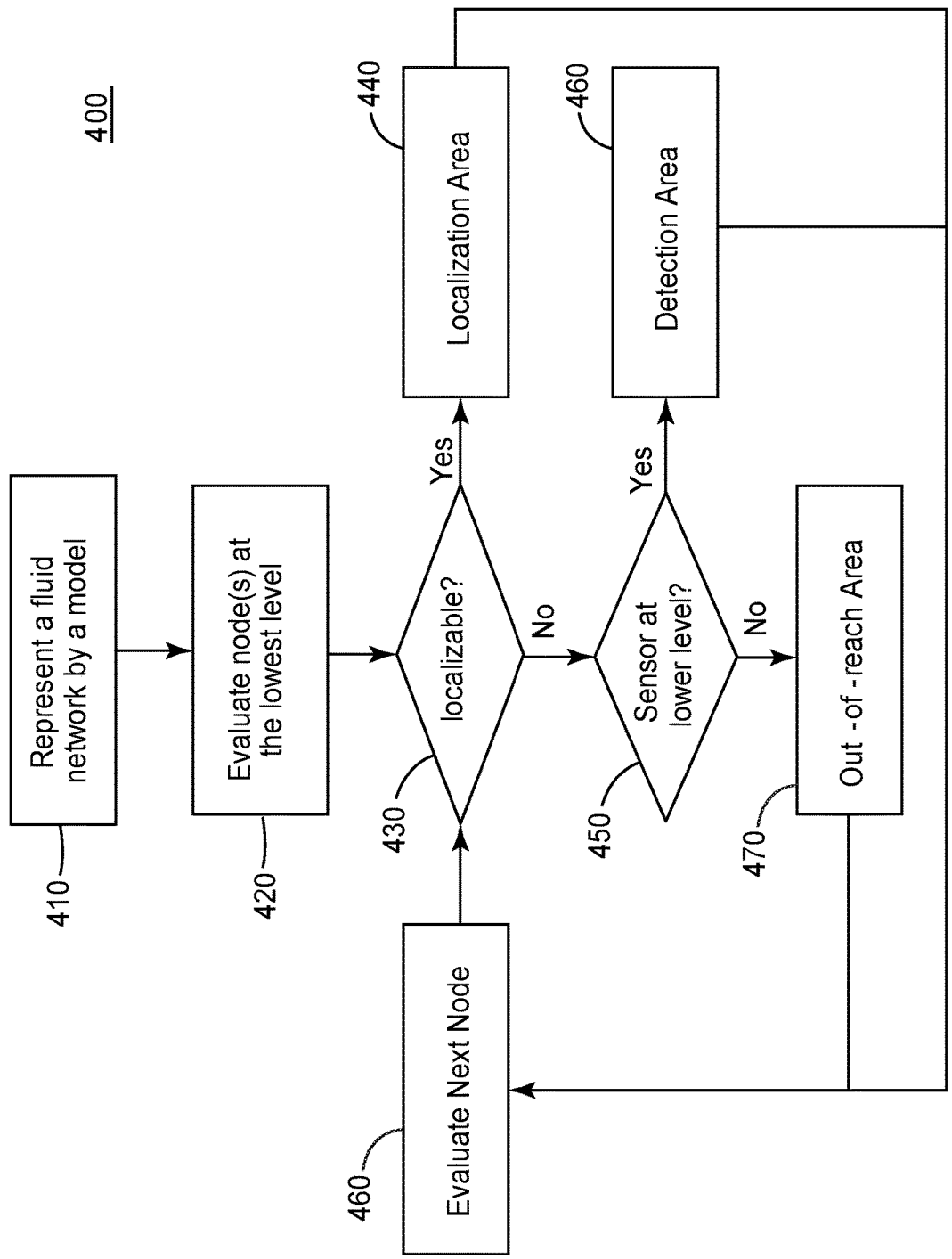
FIG. 6A illustrates a flow diagram of a method of determining sensor coverage in a fluid network, according to one embodiment.

FIG. 6A is a flow diagram of a method 400 for determining sensor coverage in a fluid network, according to one embodiment. At 410, a fluid network is represented by a model. The model can be, for example, a directed graph such as the directed graph 20 shown in FIG. 4A. The directed graph can be a partial order set where nodes are ordered in different levels. The method 400 then proceeds to 420. At 420, one or more nodes or node sets at the lowest level of the model are evaluated to determine at 430 whether the node or node set satisfies localizability criteria, e.g., whether there are at least two sensors disposed downstream of the given node or node set which have the respective paths not sharing any d-separator with respect to the given node or node set.

When the node or node set satisfies the localization criteria, the method 400 proceeds to 440. When the node or node set does not satisfy the localizability criteria, the method 400 proceeds to 450. At 440, the node or node set is assigned to a localization area. The method 400 then proceeds to 480.

At 450, the node or node set is further evaluated to determine there are sensor(s) at the node or node set or at lower level(s) (i.e., downstream of the node or node set). When there is a sensor located at or downstream of the node or node set, the method 400 proceeds to 460. At 460, the node or node set is assigned to a detection area. When there are no sensors located at or downstream of the node or node set, the method 400 proceeds to 470. At 470, the node or node set is assigned to an out-of-reach area. The method 400 then proceeds to 480.

At 480, next mode or mode set at the same level or an upper level in the model is evaluated in the same manner. The process continues until the node(s) at the upper most level of the fluid network is evaluated.

Figure 6B:
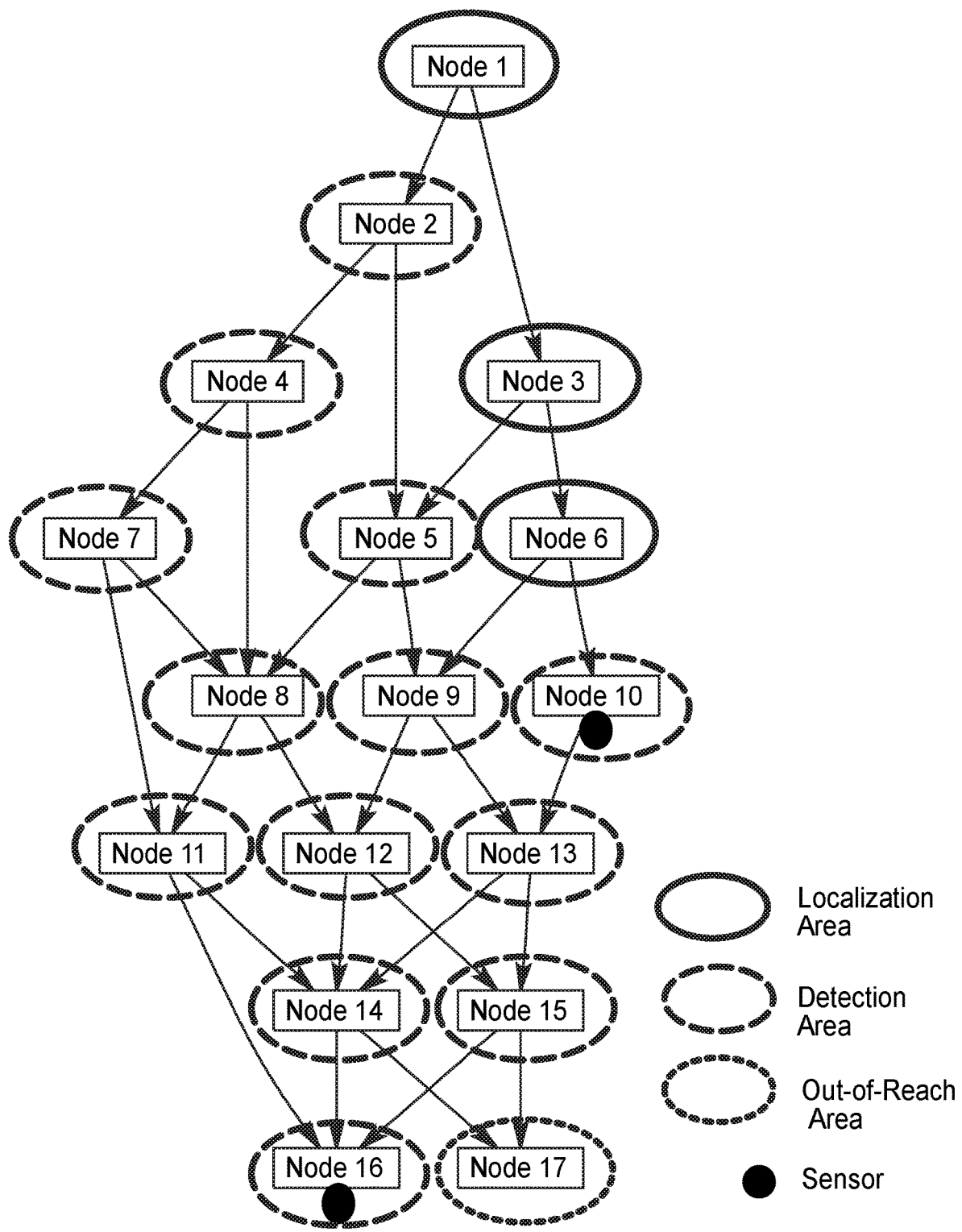
FIG. 6B illustrates a diagram of a fluid network divided into a localization area, a detection area, and an out-of-reach area, according to one embodiment.

By applying the method 400 of FIG. 6A to a fluid network represented by the model 20 of FIG. 4A, the results are shown in FIG. 6B. As shown in FIG. 6B, sensors are provided to nodes 10 and 16, respectively. The evaluation starts from the lowest level, e.g., node 16 or 17 in the directed graph 20. It is found that node 16 do not satisfy the localizability criteria. There are no sensors downstream of node 16. Node 16 is further evaluated to determine whether there is a sensor at or downstream of node 16. There is a sensor located at node 16. Node 16 is assigned to a detection area. Nodes 17 is evaluated in the same manner. It is found that node 17 do not satisfy the localizability criteria. There are no sensors downstream of node 17. Node 17 is further evaluated to determine whether there is a sensor at or downstream of node 17. There is no sensor located at or downstream of node 17. Node 17 is assigned to an out-of-reach area. Then, node 14 or 15 at the next level can be evaluated. It is found that nodes 14 and 15 do not satisfy the localizability criteria. There is only one sensor downstream at node 16. Nodes 14 and 15 are assigned to a detection area, respectively. This bottom-up approach continues and each node can be evaluated. It is found that nodes 1, 3 and 6 each satisfy the localizability criteria and assigned to a localization area. For example, for node 3, one path from node 3 to the sensor at node 16 through 3-5-9-12-14-16 and one path from node 3 to another sensor at node 10 through 3-6-10 do not share any d-separator, and node 3 satisfies the localizability criteria. Other nodes are assigned to a detection area. With sensors being placed at nodes 10 and 16, the fluid network 20 is partially covered, and divided into the localization area, the detection area, and the out-of-reach area. By analyzing the data from the sensors located at node 10 and 16, a processor of a detection system can (i) explicitly determine the location of anomaly if the anomaly source is within the localization area, and (ii) detect the occurrence of an anomaly if the anomaly source is within the detection area.

Figure 6C:
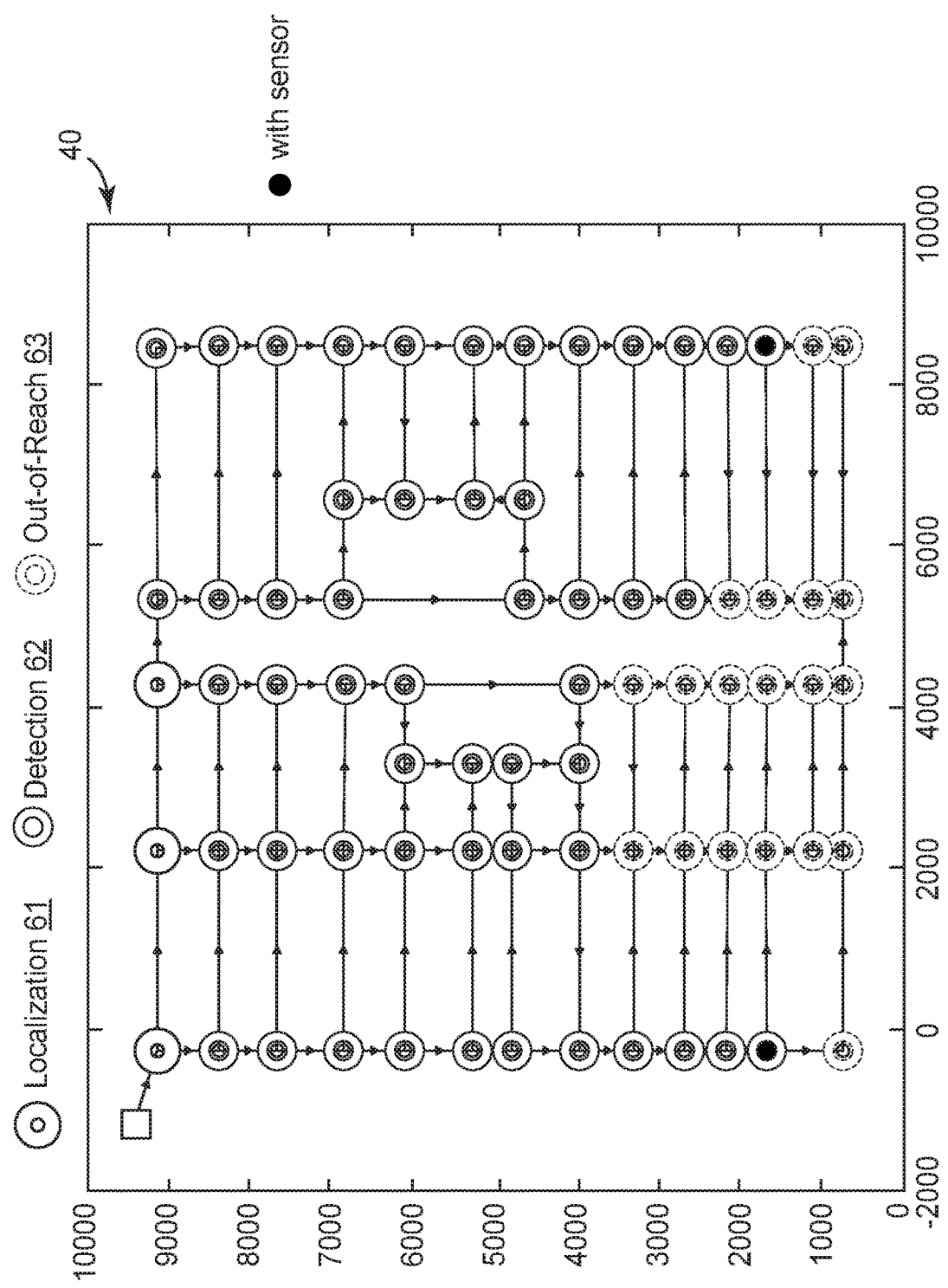
FIG. 6C illustrates a diagram of a fluid network divided into a localization area, a detection area, and an out-of-reach area, according to another embodiment.

FIG. 6C illustrates a diagram of a model 40 where the nodes are assigned to a localization area 61, a detection area 62, and an out-of-reach area 63, respectively, according to one embodiment. The model 40 of FIG. 6A are the same as the model 30 of FIG. 5B except that the number of sensors and their locations are different. Sensors are provided for the fluid network in FIG. 5B such that the whole fluid network is completely covered, while in FIG. 6C, the fluid network is partially covered and the nodes are assigned to one of a localization area, a detection area, and an out-of-reach area.

FIG. 6D illustrates a diagram of a model 50 where the nodes are assigned to a localization area 61, a detection area 62, and an out-of-reach area 63, respectively, according to another embodiment. The model 50 of FIG. 6B are the same as the model 40 of FIG. 6C except that the number of sensors and their locations are different. In FIG. 6D, the fluid network is partially covered and the nodes are assigned to one of a localization area, a detection area, and an out-of-reach area. As compared to FIG. 6C, when the number and/or location of sensors change, the assignment of the nodes to different areas is changed accordingly.

The present disclosure further provides methods of detecting and localizing an anomaly of interest in a fluid network. The anomaly can be, for example, a contamination, infrastructure fault, etc. The methods can determine the level of contamination and its location (e.g., at which node of the fluid network) when the contamination occurs within a localization area of the fluid network. The methods can further detect the occurrence/existence of contamination at other nodes (e.g., nodes in a detection area of the fluid network) and identify the locations at high risk within the fluid network.

The methods may include, for example, providing one or more sensors disposed at one or more selected locations in the fluid network. The sensors are configured to collect data from the fluid network at the respective locations. Data can be collected, via the one or more sensors, from the fluid network at the one or more locations on which the one or more sensors are disposed. The collected data can include sensor measurements before and after an anomaly has occurred. The data can then be received from the sensors, and analyzed, via the processor, based on a model of the fluid network. The model can include directionally connected nodes. In some embodiments, one or more imaginary nodes can be added between two adjacent nodes to generate a harmonic function of contamination concentration or concentration change based on the model.

Figure 7:
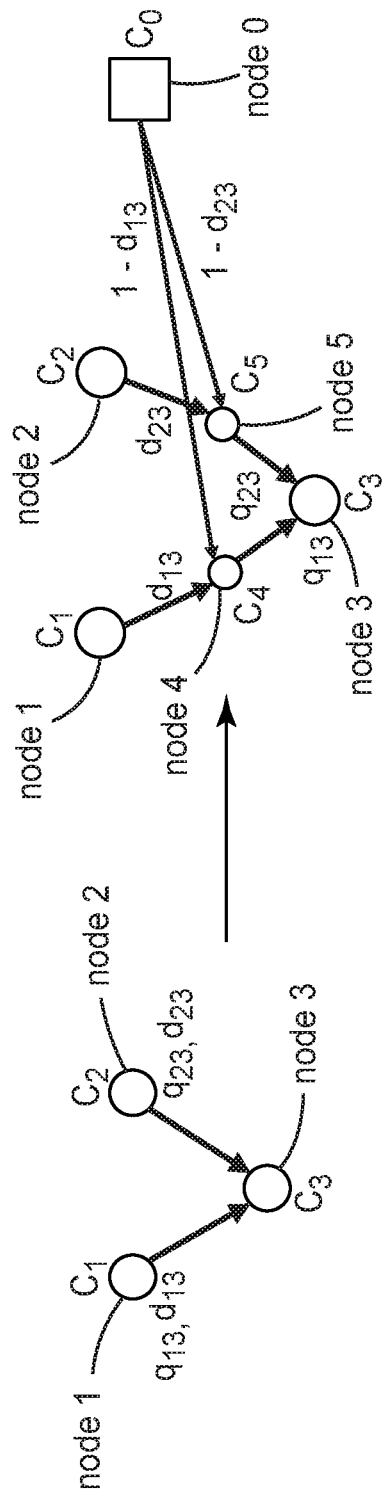
FIG. 7 illustrates a directed graph representing a fluid network modified by adding imaginary nodes, according to one embodiment.

FIG. 7 illustrates a method of modeling a fluid network by adding imaginary or decay nodes, according to one embodiment. The model of the simplified fluid network includes nodes 1 and 2 directionally connected to node 3. Imaginary nodes 4 and 5 are added between the nodes 1 and 3, and the nodes 2 and 3, respectively. Without the imaginary nodes, the concentration of contaminants (e.g., chlorine) can be expressed by:

$$C_3=(q_{13}d_{13}C_1+q_{23}d_{23}C_2)/(q_{13}+q_{23}) \quad (1a)$$

where $C_i$ is the concentration of contaminant at node i, $q_{ij}$ is a fluid flow rate from node i to j, $d_{ij}$ is a contamination decay parameter from node i to j.

The above equation (1a) is not harmonic, and there may be no-existing, not unique, or inefficient solutions.

By adding the imaginary nodes (e.g., nodes 0, 4 and 5), contamination levels (e.g., chlorine level) at the real nodes (e.g., nodes 1-3) of the fluid network can be calculated as one or more harmonic functions. The contamination decay, d, is set to zero at imaginary node 0. Then, for example, $C_4$ may be represented as:

$$C_4=(C_1d_{13}+C_0(1-d_{13}))/d_{13}+(1-d_{13}) \quad (1b)$$

Which can then reduce to the harmonic function:

$$C_4=C_1d_{13} \quad (1C)$$

This formulation may then be derived for the remaining nodes to gain a harmonic diffusion model. Given this harmonic diffusion model, and following Dirichlet's principle, the contamination level of all real nodes may be found when the contamination level (e.g., chlorine level) at the sources (originating node and any nodes with a sensor) is known.

The contamination level at the imaginary or decay nodes can be set to be about zero. In some embodiments, when the location and centration of a contamination source are determined, the contamination levels at other nodes (e.g., nodes in a detection area of the fluid network) of the fluid network can be calculated by:

$$C_{interior}=QC_{boundary} \quad (2)$$

where $C_{interior}$ is the vector of contamination levels of all nodes except for the contamination source, $C_{boundary}$ is the vector of contamination level at the contamination source, and Q is an absorption probability matrix which can be determined by a transition probability matrix. The transition probability matrix can be determined from an adjacency matrix constructed from weights, representative of fluid flow and contamination decay in the fluid network. The transition probability matrix is further partitioned to represent interior and boundary sources. The absorption probability matrix, Q, can be solved for a specific fluid network by one skilled in the art.

In some embodiments, a model of fluid network with imaginary nodes can be used to determine the location of one or more contamination sources based on data collected by sensors at some nodes, which can be further used to estimate contamination levels at other nodes and/or identify locations of contamination in high risk.

In some embodiments, for a relatively simple fluid network, the location of a contamination source can be determined by individually considering each node as a boundary node with an assumed contamination level as potential contamination source, and comparing these modeled values to the sensor measurements. For relatively complex fluid networks, this method may be difficult to implement due to the complexity of the network.

In some embodiments, the location of a contamination source can be determined by placing at least two sensors at downstream locations of the fluid network, analyzing data from the sensors before and after an anomalous event, and modeling the initial, non-anomalous state of a node. An absorption probability matrix and the contamination level at the anomaly source can then be obtained using a fitting estimation method, such as, a Least-Squares method, which is known in the art.

In some embodiments, data from the sensors can be analyzed to compute the level of contamination at nodes within a detection area of the fluid network. The methods of assigning nodes to a detection area has been discussed above. See, for example, FIG. 6B. The contamination levels at the nodes can be computed by determining an absorption probability matrix Q. The data can be further analyzed to localize one or more potential contamination sources based on the computed level of contamination at the nodes. Based on the information of the potential contamination sources, contamination levels at other nodes in the fluid network can be further estimated.

Figure 8A:
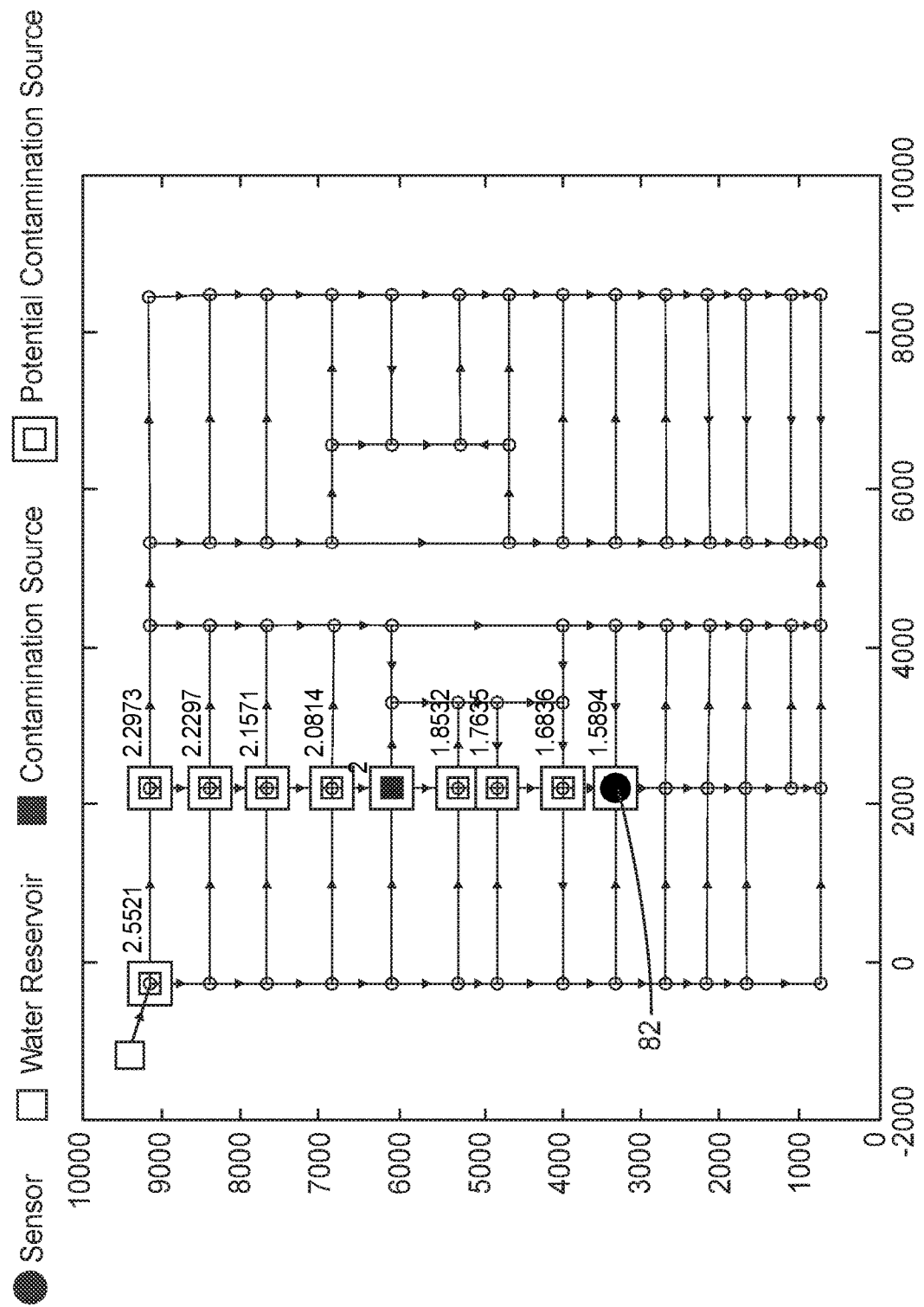
FIG. 8A illustrates a model of a fluid network to determine potential contamination source, according to one embodiment.
Figure 8B:
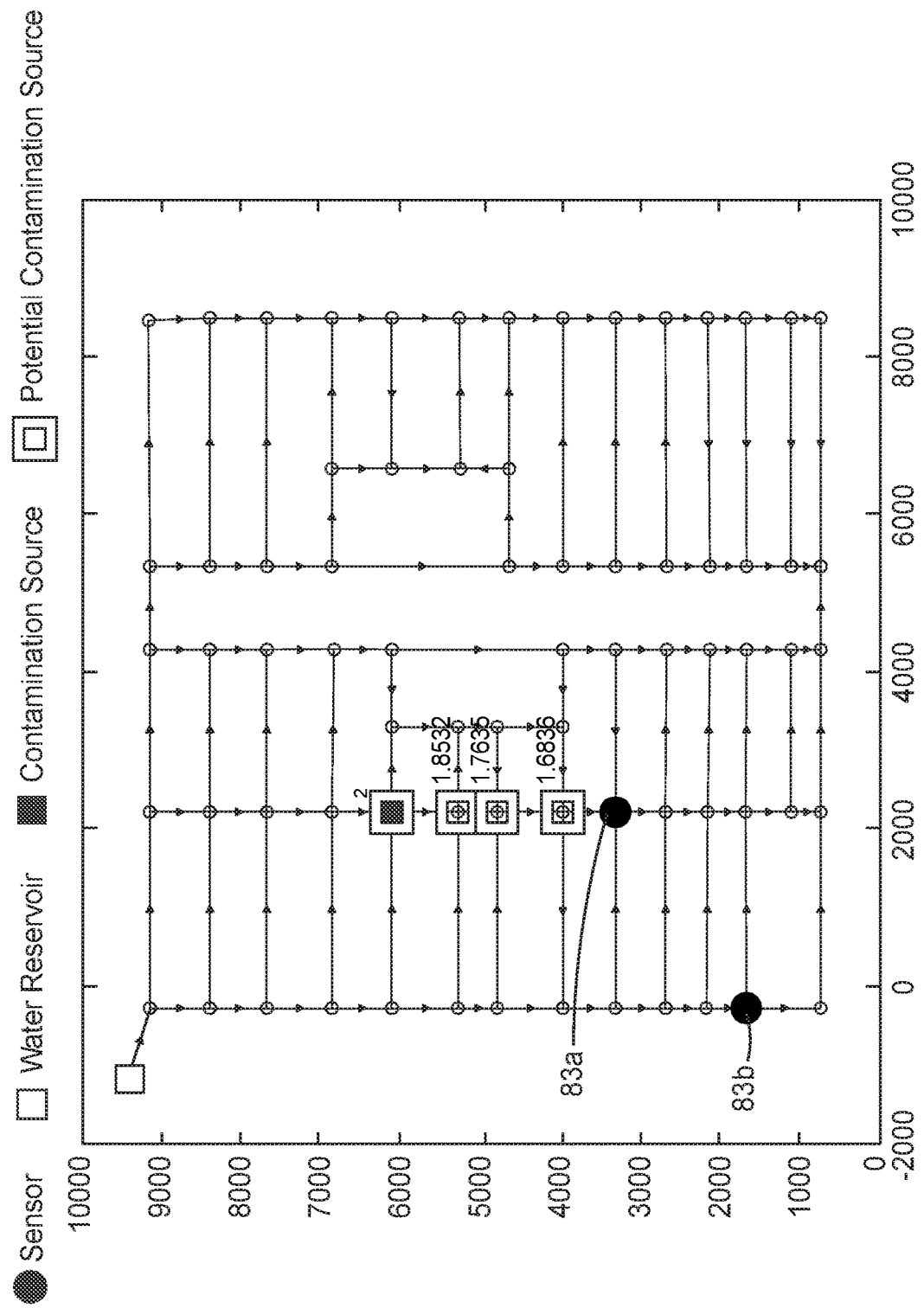
FIG. 8B illustrates a model of a fluid network to determine potential contamination source, according to another embodiment.
Figure 8C:
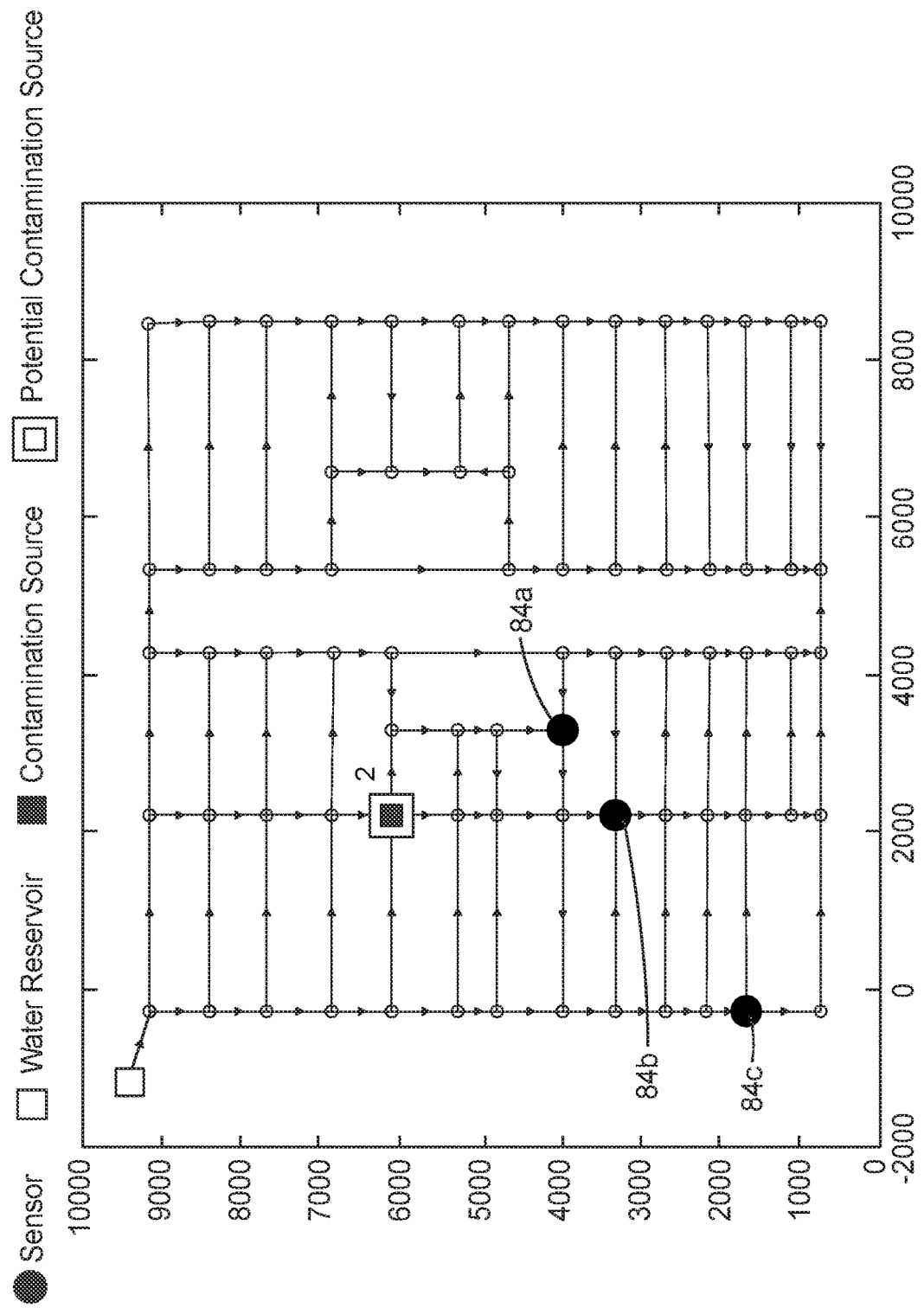
FIG. 8C illustrates a model of a fluid network to determine potential contamination source, according to another embodiment.

FIGS. 8A-C illustrate how to determine the location of contamination sources with varying amounts of sensors in a fluid network. In FIG. 8A, one sensor is located at node 82 and the contamination level is measured at the node 82. Using the model and contamination localization method discuss above, the nodes of the fluid network can be respectively assigned to a localization area, a detection area, and an out-of-reach area. The contamination levels for the nodes within the detection area can be calculated to determine potential contamination source(s). In this case, ten nodes (e.g., nodes with a square in FIG. 8A) are identified as potential contamination sources, and are labeled with their respective contamination levels. In FIG. 8B, two sensors are located at nodes 83a and 83b, respectively. Similarly, the contamination levels for the nodes within the detection area can be obtained. In this case, four nodes have been identified as a potential contamination source, and are labeled with their respective contamination levels. In FIG. 8C, three sensors are located at nodes 84a, 84b and 84c, respectively. In this case, the location of contamination source is determined to be at node 88. In FIGS. 8A-B, a contamination to a subset of localized nodes can be determined based on the calculated contamination levels and sensor(s) locations, while in FIG. 8C, the described method can exactly localize the node with the contamination source.

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

Exemplary embodiments of the present disclosure may take on various modifications and alterations without departing from the spirit and scope of the present disclosure. Accordingly, it is to be understood that the embodiments of the present disclosure are not to be limited to the following described exemplary embodiments, but is to be controlled by the limitations set forth in the claims and any equivalents thereof.

LISTING OF EXEMPLARY EMBODIMENTS

Exemplary embodiments are listed below. It is to be understood that any of embodiments in lists I, II, III and IV can be combined.

Embodiment List I

Embodiment 1 is a method of optimally determining sensor or infrastructure placement in a fluid network, the method comprising:
creating a model of the fluid network, wherein the model comprises i) a plurality of directionally connected nodes representing fluid infrastructure disposed in the fluid network, and ii) one or more sensors positioned at one or more selected locations in the fluid network;
representing the model as a matrix data structure associated with a processor, wherein the processor is disposed outside of the fluid network;
analyzing, via the processor, the matrix to evaluate whether each node of the model satisfies one or more localizability criteria, wherein analyzing the matrix comprises interpreting and executing a plurality of instructions associated with the processor; and
determining the sensor or infrastructure placement in the fluid network based on results of analyzing the matrix.
Embodiment 2 is the method of embodiment 1, wherein the model includes one or more directed acyclic graphs (DAGs), and the matrix includes a reachability matrix.
Embodiment 3 is the method of embodiment 1 or 2, wherein analyzing the matrix comprises dynamic programming including a bottom-up approach starting from the lowest level in the matrix.
Embodiment 4 is the method of any one of embodiments 1-3, wherein analyzing whether each node of the model satisfies one or more localizability criteria includes for a given node, evaluating whether there are at least two sensors disposed downstream of the given node which have the respective paths not sharing any d-separator with respect to the given node.
Embodiment 5 is the method of any one of embodiments 1-4, wherein determining the sensor or infrastructure placement comprises when a given node does not satisfy the localizability criteria, providing a sensor to the given node, and when the given node satisfies the localizability criteria, not providing a sensor to the given node.
Embodiment 6 is the method of any one of embodiments 1-5, wherein determining the sensor or infrastructure placement comprises determining the minimum number of sensors for covering the whole fluid network.
Embodiment 7 is the method of embodiment 6, wherein determining the sensor or infrastructure placement comprises determining a complexity index of the fluid network as the ratio of the minimum number of required sensors and the number of nodes.
Embodiment 8 is the method of any one of embodiments 1-7, wherein creating the model further comprises grouping a plurality of adjacent nodes of the model into a node set.
Embodiment 9 is the method of any one of embodiments 1-8, wherein determining the sensor or infrastructure placement comprises adding one or more fluid paths between the nodes in the fluid network to reduce the number of sensors.

Embodiment List II

Embodiment 1 is a method of determining an anomaly of interest in a fluid network, the method comprising:
providing one or more sensors disposed at one or more selected locations in the fluid network, wherein the sensors are configured to collect data from the fluid network at the respective locations;
collecting, via the one or more sensors, data from the fluid network at the one or more locations;
receiving, via a processor, the data from the sensors; and
analyzing, via the processor, the data based on a model of the fluid network, wherein the model is represented as a directed graph associated with the processor, the directed graph comprises a plurality of directionally connected nodes where one or more imaginary nodes are added between two adjacent nodes.
Embodiment 2 is the method of embodiment 1, wherein the anomaly is related to contamination or infrastructure fault in the fluid network.
Embodiment 3 is the method of embodiment 1 or 2, wherein analyzing the data further comprises computing the level of contamination at one or more nodes in a detection area in the fluid network.
Embodiment 4 is the method of embodiment 3, wherein computing the level of contamination at the plurality of nodes further comprises determining an absorption probability matrix Q.
Embodiment 5 is the method of embodiment 3 or 4 wherein analyzing the data further comprises localizing one or more contamination sources based on the computed level of contamination at the first nodes.
Embodiment 6 is the method of embodiment 3, 4 or 5, wherein the detection area is determined based on one or more localizability criteria including for a given node, evaluating whether there are at least two sensors disposed downstream of the given node which have the respective paths not sharing any d-separator with respect to the given node.
Embodiment 7 is the method of any one of embodiments 1-6, wherein the model is a harmonic model, and a contamination concentration level in the fluid network is represented as a harmonic function.
Embodiment 8 is the method of embodiment 7, wherein the contamination concentration level includes a chlorine level.
Embodiment 9 is the method of any one of embodiments 1-8, wherein the directed graph further comprises a second imaginary node connected to the one or more imaginary nodes.

Embodiment List III

Embodiment 1 is a method of determining sensor coverage in a fluid network, the method comprising:
creating a model of the fluid network, wherein the model comprises a plurality of directionally connected nodes representing fluid infrastructure disposed in the fluid network and one or more sensors at positioned one or more selected locations in the fluid network;
representing the model as a matrix data structure associated with a processor, wherein the processor is disposed outside of the fluid network;
analyzing, via the processor, the matrix to evaluate whether each node satisfies one or more localizability criteria, wherein analyzing the matrix comprises interpreting and executing a plurality of instructions associated with the processor; and assigning each node to one of a localization area, a detection area, and an out-of-reach area.
Embodiment 2 is the method of embodiment 1, wherein the model is a graphical model including one or more directed acyclic graphs (DAGs).

Embodiment 3 is the method of embodiment 1 or 2, wherein analyzing whether each node satisfies one or more localizability criteria comprises evaluating, via the plurality of instructions, paths between a pair of nodes to determine whether the paths pass through a medial node.

Embodiment 4 is the method of embodiment 3, wherein evaluating the path includes implementing, via the plurality of instructions, an advanced Markov chain method.

Embodiment 5 is the method of any one of embodiments 1-4, wherein analyzing whether each node satisfies one or more localizability criteria includes for a given node, evaluating, via the plurality of instructions, whether there are at least two sensors downstream of the given node which have the respective paths not sharing any d-separator with respect to the given node.

Embodiment 6 is the method of any one of embodiments 1-5, wherein when a given node satisfies the localizability criteria, the given node is assigned to the localization area, and when the given node does not satisfy the localizability criteria, the given node is assigned to the detection area or the out-of-reach area.

Embodiment 7 is the method of embodiment 6, wherein when the given node does not satisfy the localizability criteria, the given node is further evaluated to determine whether a sensor is located downstream from the given node, when no sensors are located downstream, the given node is assigned to the out-of-reach area, otherwise the given node is assigned to the detection area.

Embodiment 8 is the method of any one of embodiments 1-7 further comprising determining a minimum detectable concentration of contamination level for each node.

Embodiment 9 is the method of embodiment 8, wherein determining the minimum detectable concentration comprises analyzing the sensitivity of sensors distributed in the fluid network and an absorption probability matrix.

Embodiment List IV

Embodiment 1 is a system, comprising:
one or more sensors positioned at one or more selected locations in a fluid network, wherein the sensors are configured to collect data from the fluid network at the respective locations; and
a processor disposed outside of the fluid network, wherein the processor is configured to receive the data from the sensors, and analyze the data based on a model of the fluid network, wherein the model comprises a plurality of directionally connected nodes representing fluid infrastructure disposed in the fluid network and one or more sensors positioned at the one or more selected locations; and
a plurality of instructions associated with the processor, wherein the plurality of instructions are interpretable and executable by the processor to analyze the data and determine sensor placement within the fluid network.

Embodiment 2 is the system of embodiment 1, wherein the fluid network includes a water network.

Embodiment 3 is the system of embodiment 1 or 2, wherein the fluid infrastructure of the fluid network includes one or more water filters.

Embodiment 4 is the system of embodiment 3, wherein the plurality of sensors includes one or more filter sensors provided with the water filters.

Embodiment 5 is the system of any one of embodiments 1-4, wherein the data from the sensors are related to one or more parameters of a disinfectant concentration, a contaminant concentration, a pressure, or a flow rate.

Embodiment 6 is the system of any one of embodiments 1-5, wherein the data are related to a change or damage to the fluid network.

Embodiment 7 is the system of any one of embodiments 1-6 further comprising a database associated with the processor, wherein the data from the sensors are stored in the database.

Embodiment 8 is the system of embodiment 7, wherein the database further includes historical data related to the model of the fluid network.

Embodiment 9 is the system of any one of embodiments 1-8 further comprising a display.

Embodiment 10 is the system of any one of embodiments 1-9, wherein the model includes one or more directed acyclic graph (DAGs).

Reference throughout this specification to "one embodiment," "certain embodiments," "one or more embodiments," or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment," or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g., 1 to 5 includes 1, 1.5, 2, 2.75, 3, 3.80, 4, and 5). In addition, all numbers used herein are assumed to be modified by the term "about."

Furthermore, various exemplary embodiments have been described. These and other embodiments are within the scope of the following claims.

What is claimed is:

1. A method of determining sensor coverage in a fluid network, the method comprising:
creating a model of the fluid network, wherein the model comprises a plurality of directionally connected nodes representing fluid infrastructure disposed in the fluid network and one or more sensors at positioned one or more selected locations in the fluid network;
representing, via a processor, the model as a computer data structure comprising a matrix data structure, wherein the processor is disposed outside of the fluid network;
collecting sensor data comprising a contamination concentration or concentration change from one or more sensors disposed at one or more selected locations of the nodes in the fluid network;
analyzing, via the processor, the matrix data structure to evaluate whether each node of the fluid network satisfies one or more localizability criteria, wherein analyzing the matrix comprises interpreting and executing a plurality of instructions implemented by the processor;

assigning each node to one of a localization area, a detection area, and an out-of-reach area;

generating, via the processor, a harmonic function of the contamination concentration or concentration change;

modifying, via the processor, the matrix data structure to a harmonic diffusion model based on the harmonic function; and calculating and outputting, via the processor, a contamination level at each of the nodes in the fluid network based on the harmonic diffusion model.

2. The method of claim 1, wherein the model is a graphical model including one or more directed acyclic graphs (DAGs).

3. The method of claim 1, wherein analyzing whether each node satisfies one or more localizability criteria comprises evaluating, via the plurality of instructions, paths between a pair of nodes to determine whether the paths pass through a medial node.

4. The method of claim 3, wherein evaluating the path includes implementing, via the plurality of instructions, an advanced Markov chain method.

5. The method of claim 1, wherein analyzing whether each node satisfies one or more localizability criteria includes for a given node, evaluating, via the plurality of instructions, whether there are at least two sensors located downstream of the given node which have the respective paths not sharing any d-separator with respect to the given node.

6. The method of claim 1, wherein when a given node satisfies the localizability criteria, the given node is assigned to the localization area, and when the given node does not satisfy the localizability criteria, the given node is assigned to the detection area or the out-of-reach area.

7. The method of claim 6, wherein when the given node does not satisfy the localizability criteria, the given node is further evaluated to determine whether a sensor is located downstream from the given node, when no sensors are located downstream, the given node is assigned to the out-of-reach area, otherwise the given node is assigned to the detection area.

8. The method of claim 1 further comprising determining a minimum detectable concentration of contamination level for each node.

9. The method of claim 8, wherein determining the minimum detectable concentration comprises analyzing the sensitivity of sensors distributed in the fluid network and an absorption probability matrix.

10. A system, comprising:

one or more sensors positioned at one or more selected locations in a fluid network, wherein the sensors are configured to collect data comprising a contamination concentration or concentration change from the fluid network at the respective locations; and a processor disposed outside of the fluid network, wherein the processor is configured to receive the data from the sensors, and analyze the data based on a model of the fluid network, wherein the model is represented as a computer data structure comprising a plurality of directionally connected nodes representing fluid infrastructure disposed in the fluid network and the one or more sensors positioned at the one or more selected locations, wherein a plurality of instructions are interpretable and executable by the processor to analyze the data and determine sensor placement within the fluid network, and wherein the processor is further configured to:

generate a harmonic function of the contamination concentration or concentration change;

modify the model to a harmonic diffusion model based on the harmonic function; and calculate and output a contamination level at each of the nodes in the fluid network based on the harmonic diffusion model.

11. The system of claim 10, wherein the fluid network includes a water network.

12. The system of claim 10, wherein the fluid infrastructure of the fluid network includes one or more water filters.

13. The system of claim 12, wherein the plurality of sensors includes one or more filter sensors provided with the water filters.

14. The system of claim 10, wherein the data from the sensors are related to one or more parameters of a disinfectant concentration, a contaminant concentration, a pressure, or a flow rate.

15. The system of claim 10, wherein the data are related to a change or damage to the fluid network.

16. The system of claim 10 further comprising a database associated with the processor, wherein the data from the sensors are stored in the database.

17. The system of claim 16, wherein the database further includes historical data related to the model of the fluid network.

18. The system of claim 10 further comprising a display.

19. The system of claim 10, wherein the model includes one or more directed acyclic graph (DAGs).

* * * * *